(12) United States Patent
Autar et al.

(10) Patent No.: US 12,419,582 B2
(45) Date of Patent: Sep. 23, 2025

(54) SMART BED SYSTEM

(71) Applicant: CENTERED AROUND YOU PTY LTD, Kensington (AU)

(72) Inventors: Nikhil Autar, Voyager Point (AU); Nick Rabey, Macquarie Park (AU)

(73) Assignee: CENTERED AROUND YOU PTY LTD, Kensington (AU)

(*) Notice: Subject to any disclaimer, the term of this patent is extended or adjusted under 35 U.S.C. 154(b) by 1052 days.

(21) Appl. No.: 17/283,687

(22) PCT Filed: Oct. 10, 2019

(86) PCT No.: PCT/AU2019/051096
§ 371 (c)(1),
(2) Date: Apr. 8, 2021

(87) PCT Pub. No.: WO2020/073091
PCT Pub. Date: Apr. 16, 2020

(65) Prior Publication Data
US 2021/0345968 A1    Nov. 11, 2021

(30) Foreign Application Priority Data
Oct. 10, 2018  (AU) ................................ 2018903834

(51) Int. Cl.
*A61B 5/00* (2006.01)
*A61B 5/024* (2006.01)
(Continued)

(52) U.S. Cl.
CPC .......... *A61B 5/6892* (2013.01); *A61B 5/0004* (2013.01); *A61B 5/024* (2013.01);
(Continued)

(58) Field of Classification Search
CPC ..... A61B 5/01; A61B 5/0205; A61B 5/02055; A61B 5/0816; A61B 5/1036; A61B 5/11;
(Continued)

(56) References Cited

U.S. PATENT DOCUMENTS

| | | | |
|---|---|---|---|
| 4,104,749 A | | 8/1978 | Grundler |
| 4,195,287 A | * | 3/1980 | McCoy ................. A61B 5/1115 5/940 |

(Continued)

FOREIGN PATENT DOCUMENTS

| | | |
|---|---|---|
| CA | 1105202 | 7/1981 |
| CA | 1105202 A | 7/1981 |

(Continued)

OTHER PUBLICATIONS

Machine Translation (CN 106943258 A) (Year: 2024).*
(Continued)

*Primary Examiner* — Tse W Chen
*Assistant Examiner* — Alice Ling Zou
(74) *Attorney, Agent, or Firm* — Osha Bergman Watanabe & Burton LLP

(57) ABSTRACT

Described herein is a smart bed system, which includes a number of different elements that operate together or may operate independently in connection with an existing conventional bed frame and/or mattress. Bed system includes an inclinable bed apparatus, which is configured to be situated on an existing bed frame or mattress and provide selective inclining/reclining of a patient or user. A sensor mat system is adapted to be situated on mattress. Sensor mat system includes a plurality of different layers to sense the position and movement of a patient. An inflatable bladder system includes a plurality of inflatable cells for selectively adjusting the position or pressure experienced by a patient using bed system. A support rail system supports a user in a bed.

(Continued)

A microcontroller performs various control and data processing operations associated with system. User input for various controls of system may be provided from a remote control, which is in data communication with microcontroller.

21 Claims, 27 Drawing Sheets

(51) Int. Cl.
*A61B 5/08* (2006.01)
*A61B 5/11* (2006.01)
*A61G 7/018* (2006.01)
*A61G 7/057* (2006.01)

(52) U.S. Cl.
CPC .......... *A61B 5/0816* (2013.01); *A61B 5/1117* (2013.01); *A61B 5/4094* (2013.01); *A61B 5/4818* (2013.01); *A61B 5/7275* (2013.01); *A61B 5/746* (2013.01); *A61G 7/018* (2013.01); *A61G 7/05776* (2013.01); *A61B 2562/0247* (2013.01); *A61B 2562/0271* (2013.01)

(58) Field of Classification Search
CPC ..... A61B 5/1115; A61B 5/113; A61B 5/6843; A61B 2562/0247; A61B 5/0826; A61B 5/1102; A61B 5/1117–1118; A61B 5/4806–4818; A61B 5/6891–6892; A61B 2562/0261
See application file for complete search history.

(56) References Cited

U.S. PATENT DOCUMENTS

| | | | |
|---|---|---|---|
| 4,715,073 A | 12/1987 | Butler | |
| 5,144,284 A * | 9/1992 | Hammett | A61B 5/6892 340/573.5 |
| 7,240,385 B1 | 7/2007 | Brown | |
| 8,950,026 B2 * | 2/2015 | Valdemoros Tobia | A61B 5/447 5/613 |
| 8,997,588 B2 | 4/2015 | Taylor | |
| 2004/0046668 A1 * | 3/2004 | Smith | A61B 5/6892 340/573.7 |
| 2004/0111015 A1 * | 6/2004 | Ladd | A61B 5/6892 600/300 |
| 2006/0065060 A1 * | 3/2006 | Ito | G01D 7/00 73/862.046 |
| 2007/0008156 A1 * | 1/2007 | Ueda | A47C 20/04 340/575 |
| 2007/0205701 A1 * | 9/2007 | Grumm | A61B 5/4818 310/800 |
| 2008/0275349 A1 * | 11/2008 | Halperin | A61B 5/447 600/364 |
| 2009/0084609 A1 | 4/2009 | Skinner et al. | |
| 2009/0289800 A1 * | 11/2009 | Hansen | A61B 5/1115 340/666 |
| 2010/0024132 A1 | 2/2010 | Carlson et al. | |
| 2010/0245090 A1 * | 9/2010 | Smith | H10N 10/854 340/573.1 |
| 2011/0112442 A1 * | 5/2011 | Meger | A61B 5/7203 600/595 |
| 2011/0224510 A1 * | 9/2011 | Oakhill | A61B 5/4815 600/301 |
| 2011/0279276 A1 * | 11/2011 | Newham | A61B 5/6892 340/573.4 |
| 2014/0039351 A1 * | 2/2014 | Mix | G16H 40/20 600/587 |
| 2014/0090489 A1 * | 4/2014 | Taylor | G01L 1/00 73/862.626 |
| 2015/0119656 A1 * | 4/2015 | Foster | A61B 5/746 600/301 |
| 2015/0309563 A1 * | 10/2015 | Connor | A61B 5/1071 73/865.4 |
| 2015/0358017 A1 * | 12/2015 | Lin | H03K 17/162 327/384 |
| 2016/0100696 A1 * | 4/2016 | Palashewski | A61B 5/6892 5/706 |
| 2017/0234723 A1 * | 8/2017 | Charles | G01G 23/01 5/600 |
| 2018/0042556 A1 | 2/2018 | Shahparnia et al. | |
| 2018/0125256 A1 * | 5/2018 | Tsern | G05B 13/0265 |
| 2019/0008708 A1 * | 1/2019 | Moreno | G06F 3/0489 |
| 2019/0029900 A1 * | 1/2019 | Walton | A61G 7/015 |

FOREIGN PATENT DOCUMENTS

| | | | |
|---|---|---|---|
| CN | 106943258 A * | 7/2017 | .......... A61B 5/6892 |
| EP | 1949822 A1 | 7/2008 | |
| IT | BO20090408 | 12/2010 | |
| WO | 2009120270 A2 | 10/2009 | |

OTHER PUBLICATIONS

Extended European Search Report 19871775.3 Issued on Nov. 8, 2021 and Chinese Office Action 201980068346.6 Issued on Nov. 5, 2021.

* cited by examiner

SMART BED SYSTEM

CROSS-REFERENCE TO RELATED PATENT APPLICATIONS

The present application is a U.S. national stage application under 35 U.S.C. § 371 of PCT Application No. PCT/AU2019/051096, filed Oct. 10, 2019, which claims priority from Australian Patent Application No. 2018903834, filed on Oct. 10, 2018, the entire disclosures of which are incorporated herein by reference.

FIELD OF THE INVENTION

The present application relates to a bed system and in particular to an inclining bed apparatus configured to be situated on a bed frame, an inflatable bladder system, sensor mat system, support rail system and a bed system.

Embodiments of the present invention are particularly adapted for use with patients of a treatment facility such as a hospital or clinic. However, it will be appreciated that the invention is applicable in broader contexts and other applications such as with everyday users in the home setting.

BACKGROUND

Patients in hospitals and treatment facilities often succumb to complications such as falls and bed sores. These are a common occurrence not only to injured patients, but also to people with temporary or permanent disabilities and senior members of society. These problems are secondary in nature as they are not the initial cause of injury to a person but arise from complications of a person's circumstances or treatment environment. However, they are of primary importance as they occur regularly and give rise to injury, prolonged hospital recovery time and even death.

Apart from the personal hardship these complications can cause, they also place additional burden on the health care system, leading to higher cost of healthcare and reduced resources for others needing care.

Currently, preventable problems like falls and bed sores are addressed using complex hospital bed systems combined with regular monitoring by professionals. The equipment required is costly and complex to maintain. Further, the operation and monitoring typically requires extended periods in the presence of primary or secondary health care professionals.

Furthermore, millions around the world suffer from subpar sleep, and insomnia due to a range of conditions. However, currently, monitoring of parameters of a person during sleep, such as movement, breathing, heart rates and more, is expensive and laborious in the case of sleep lab studies, or else invasive, inaccurate and mere estimations in the case of home monitoring or wearable devices.

Any discussion of the background art throughout the specification should in no way be considered as an admission that such art is widely known or forms part of common general knowledge in the field.

SUMMARY OF THE INVENTION

In accordance with a first aspect of the present invention, there is provided an inclinable bed apparatus configured to be situated on a bed frame, the bed apparatus including:
  a base for supportively engaging with the bed frame or a mattress thereof;
  a support arm hingedly attached to the base and adapted to engage a support substrate for supporting a user; and
  an actuation system configured to selectively rotate the support arm relative to the base between a number of predefined angular positions.

In some embodiments, the base includes at least one longitudinally extending base member that extends at least partially along a length of the bed frame. In some embodiments, the support arm includes at least one longitudinally extending support member that extends at least partially along a length of the bed frame. Preferably the base includes a plurality of longitudinally extending base members that extend at least partially along the length of the bed frame. Preferably the support arm includes a plurality of longitudinally extending support members that extend at least partially along the length of the bed frame.

In some embodiments, the support arm includes a plurality of substantially planar support panels releasably engageable with the longitudinally extending support members. In some embodiments, the planar support panels include engagement apertures on one side and engagement projections on another side, the engagement apertures being configured to receive corresponding engagement projections from an adjacent support panel.

In some embodiments, at least a subset of the longitudinally extending base members are longitudinally adjustable in length. In some embodiments, at least a subset of the longitudinally extending base members are telescopically adjustable in length.

In some embodiments, the base includes three parallel disposed longitudinally extending base members and the support arm includes three parallel disposed longitudinally extending support members. In some embodiments, two outer base members are telescopically adjustable in length.

In some embodiments, the actuation system is mounted on a central base member intermediate two outer base members and the actuator system is mechanically connected to a central support member intermediate two outer support members.

In some embodiments, the base includes a lateral base member extending laterally between the longitudinally extending base members across a width of the bed frame and the support arm includes a lateral support member extending laterally between the longitudinally extending support members across the width of the bed frame.

In some embodiments, the lateral base member and the lateral support member are laterally adjustable in length. Preferably, the lateral base member and the lateral support member are telescopically adjustable in length.

In some embodiments, the base engages with the bed frame by way of straps.

In some embodiments, the two outer base members include vertically extending feet for supportively engaging an end of the support substrate. In one embodiment, the support substrate is a mattress. In another embodiment, the support substrate is an air bladder including a plurality of separately inflatable cells. Preferably the cells are disposed laterally across a surface of the bed frame. Preferably the cells are disposed in two or more vertical layers.

In some embodiments, the actuation system includes an electric linear actuator configured to linearly extend or retract an actuator arm that is connected between the base and the support arm.

In accordance with a second aspect of the present invention, there is provided an inflatable bladder system, including:
  a plurality of inflatable cells; and a gas delivery system for selectively delivering gas from a gas supply source to the cells, the delivery system including:
    one or more pumps connected to the gas supply source;
    a plurality of gas supply lines connected between the one or more pumps and at least a subset of the inflatable cells;
    a plurality of electrically actuatable valves disposed on respective ones of the gas supply lines and being responsive to electrical control signals for selectively opening or closing the valves to deliver gas to the inflatable cells; and
    an inflation microcontroller configured to generate the electrical control signals.

In some embodiments, the plurality of inflatable cells is divided into groups and each group has a corresponding electrically actuatable valve configured to supply gas along a common gas supply line to each of the cells within the group. In some embodiments, at least a subset of the inflatable cells within a group are separated by pressure valves which permit flow of gas from a first cell to a second cell upon the first cell reaching a predefined pressure threshold. In some embodiments, each cell includes a corresponding electrically actuatable valve for receiving gas along a corresponding gas supply line such that each cell is independently inflatable.

In some embodiments, the plurality of inflatable cells is divided into vertically distributed layers. In some embodiments, the plurality of inflatable cells is divided into a two dimensional horizontal array of cells. Preferably, the plurality of inflatable cells is divided into a three dimensional grid of cells.

In some embodiments, the inflation microcontroller is responsive to one or more weight or pressure sensors configured to sense a weight or pressure of a subject situated on the inflatable cells.

In some embodiments, the microprocessor is responsive to user input to generate the electrical control signals. The user input may include a wireless signal received from a remote control device. The user input may also include a voice command.

In some embodiment, the inflation microcontroller is responsive to a CPR override signal to deflate all inflatable cells.

In some embodiments, the inflatable bladder system includes a rigid layer disposed beneath the plurality of inflatable cells.

In some embodiments, at least a subset of the inflatable cells includes an internal electronic or pressure sensitive valve which permits flow of gas between adjacent cells.

Preferably the gas is air.

In some embodiments, the inflatable bladder system includes engagement straps configured to engage the inflatable bladder system with a mattress or bed frame.

In accordance with a third aspect of the present invention, there is provided a sensor mat system for a bed, the sensor mat system including:
    a first layer including a piezoelectric material surrounded by a plurality of electrically conductive elements configured to generate first pressure signals in response to an applied pressure;
    a second layer including a plurality of spatially distributed sensors configured to generate second pressure signals in response to the applied force; and
    a sensor microcontroller in electrical communication with the electrically conductive elements and the sensors to process the first and second pressure signals to generate pressure data indicative of a spatial distribution of pressure across the sensor mat.

In some embodiments, the sensor mat system includes a gel material disposed between the first and second layers.

In some embodiments, the sensors include one or more force sensitive resistors, strain gauges, load cells, capacitive transducers and/or stretch sensors.

In some embodiments, the sensor microcontroller is configured to determine a position of a subject laying on the sensor mat system based on the pressure data.

In some embodiments, the sensor microcontroller is configured to determine movement patterns of a subject laying on the sensor mat system based on the pressure data. In some embodiments, the sensor microcontroller is configured to determine movement patterns of a subject laying on the sensor mat system based on the pressure data. In some embodiments, the sensor microcontroller is configured to determine physiological signals of a subject laying on the sensor mat system based on the pressure data. In some embodiments, the sensor microcontroller is configured to predict potential pressure sores of a subject laying on the sensor mat system based on the pressure data. In some embodiments, the sensor microcontroller is configured to detect potential fall events of a subject laying on the sensor mat system based on the pressure data.

In some embodiments, the sensor mat system includes a third layer including one or more embedded moisture sensors.

In some embodiments, the sensor mat system includes a communications module for transmitting the pressure data to a remote database. In some embodiments, the sensor microcontroller is configured to generate third party alerts based on the pressure data. In some embodiments, the sensor microcontroller is configured to transmit the pressure data to the inflation microcontroller of the inflatable bladder system of the second aspect, and wherein the electrical control signals are based on the pressure data. In some embodiments, the sensor microcontroller is configured to receive electronic control signals from the inflation microcontroller of the inflatable bladder system of the second aspect, and wherein the pressure data is generated based on the received electronic control signals.

In some embodiments, the sensor microcontroller of the sensor mat system and the inflation microcontroller of the inflatable bladder system are the same.

In some embodiments, the physiological signals include a heart rate of the subject. In some embodiments, the physiological signals include a breathing rate of the subject. In some embodiments, the physiological signals are derived by performing a spectral analysis of the pressure data.

In some embodiments, the microprocessor is adapted to perform predictions of subject health conditions based on the pressure data. The health conditions may include sleep apnea. The health conditions may also include cardiac arrest. The health conditions may also include epilepsy.

In some embodiments, the second layer includes one or more of a thermometer and/or ultraviolet sensor.

In some embodiments, the sensor mat system includes one or more of a camera, UV detector or radar beam generator devices.

In some embodiments, the sensor microcontroller is configured to connect to a cloud based system which utilizes a machine learning algorithm to continuously improve alerts for pressure sore detection based on the pressure data.

In some embodiments, the sensor microcontroller is configured to connect to a cloud based system which utilizes a machine learning algorithm to perform one or more of:

Continuously improving alerts for falls detection based on the pressure data.

Continuously improving alerts for adverse conditions associated with lower breath rates based on the pressure data.

Continuously improving alerts for adverse conditions associated with fluctuating heart rates based on the pressure data.

Continuously monitoring sleep patterns based on the pressure data.

In accordance with a fourth aspect of the present invention, there is provided a bed system including:
an inclinable bed apparatus according to the first aspect;
an inflatable bladder system according to the second aspect;
a sensor mat system according to the third aspect.

In some embodiments, the bed system includes a microphone for receiving voice commands from a user and wherein the sensor microcontroller or inflation microcontroller is adapted to perform voice recognition to convert the voice commands into corresponding control signals for controlling one or both of the actuation system and electrically actuatable valves.

In some embodiments, the bed system includes one or more cover sheets which extend over the bed system to secure the system to a bed frame via one or more engagement formations, wherein the one or more cover sheets are able to function as conventional bed sheets for a user.

In some embodiments, the inflation microcontroller or sensor microcontroller is in electrical or wireless communication with a remote control device for receiving user input commands.

In some embodiments, the inflation microcontroller or sensor microcontroller is responsive to the user input commands for controlling the actuation system of the inclinable bed apparatus.

In some embodiments, the bed system includes a speaker system configured to convey audio information to a user.

In some embodiments, the bed system includes one or more electrical ports for connecting and/or charging electronic devices.

In accordance with a fifth aspect of the present invention, there is provided a support rail system for a bed, the support system including:
an engagement formation for engaging with a bed frame;
a support rail mounted to the engagement formation;
one or more support legs extending downward from the engagement formation, the support legs being adjustable in length to engage with a floor adjacent the bed to maintain the support rail in an operable position.

In some embodiments, the one or more support legs are telescopically adjustable in length. Preferably the one or more support legs are electronically telescopically adjustable in length in response to a control signal.

In some embodiments, the support rail is adjustable in height. Preferably the support rail is telescopically adjustable in height.

In some embodiments, the support rail is rotatable relative to the engagement formation via a hinge joint between an operable position and a folded position. Preferably the support rail is electronically rotatable in response to a control signal. In some embodiments, the support rail extends substantially vertically in the operable position.

In some embodiments, the engagement formation includes an engagement arm that extends substantially horizontally to be positioned under a mattress of the bed.

In some embodiments, the one or more support legs extend downwardly and outwardly from the bed. Preferably, the support rail system includes two support legs.

In some embodiments, the engagement formation is rotatable between an operable position and a folded position.

In accordance with a sixth aspect of the present invention, there is provided a mattress for use with the inflatable bladder system according to the second aspect, the mattress having an array of incisions or perforations in an underside at locations corresponding to the plurality of inflatable cells.

BRIEF DESCRIPTION OF THE FIGURES

Example embodiments of the disclosure will now be described, by way of example only, with reference to the accompanying drawings in which.

DESCRIPTION OF THE INVENTION

Figure 1:
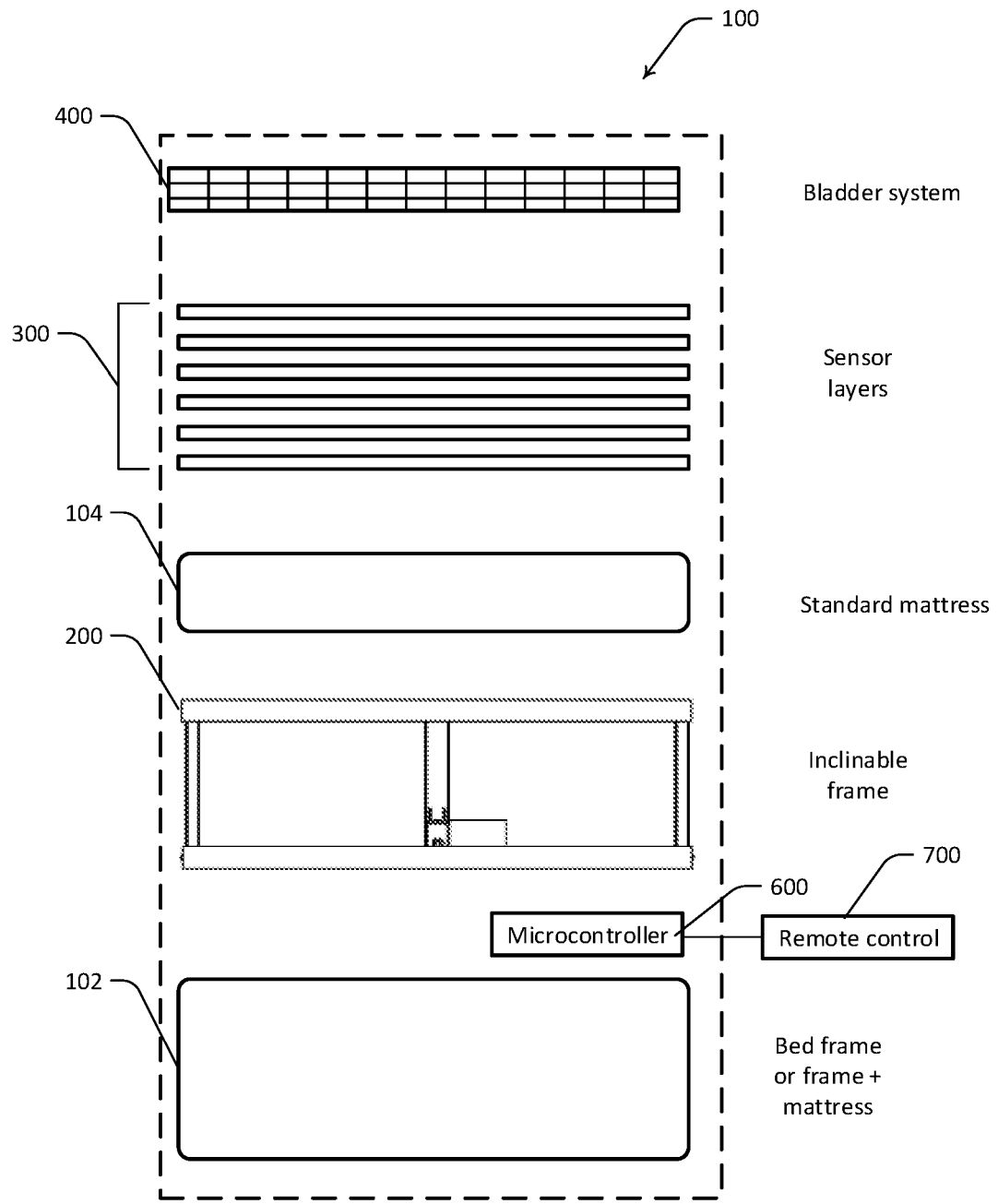
FIG. 1 is an exploded view of a smart bed system including a plurality of interoperating or independent components.

Referring initially to FIG. 1, there is illustrated an exploded view of a smart bed system 100. Bed system 100 includes a number of different elements which operate together or may operate independently in connection with an existing conventional bed frame 102 and/or mattress 104. Bed system 100 will be described herein with reference to a retro-fittable system for a bed in a treatment facility such as a hospital, clinic, nursing home or other care facility. In this regard, users of system 100 will be referred to herein as "patients". However, it will be appreciated that bed system 100 has applications in much broader contexts such as everyday consumer use in the home setting. Thus, more generally, patients may be referred to simply as "users" of the system.

Figure 23:
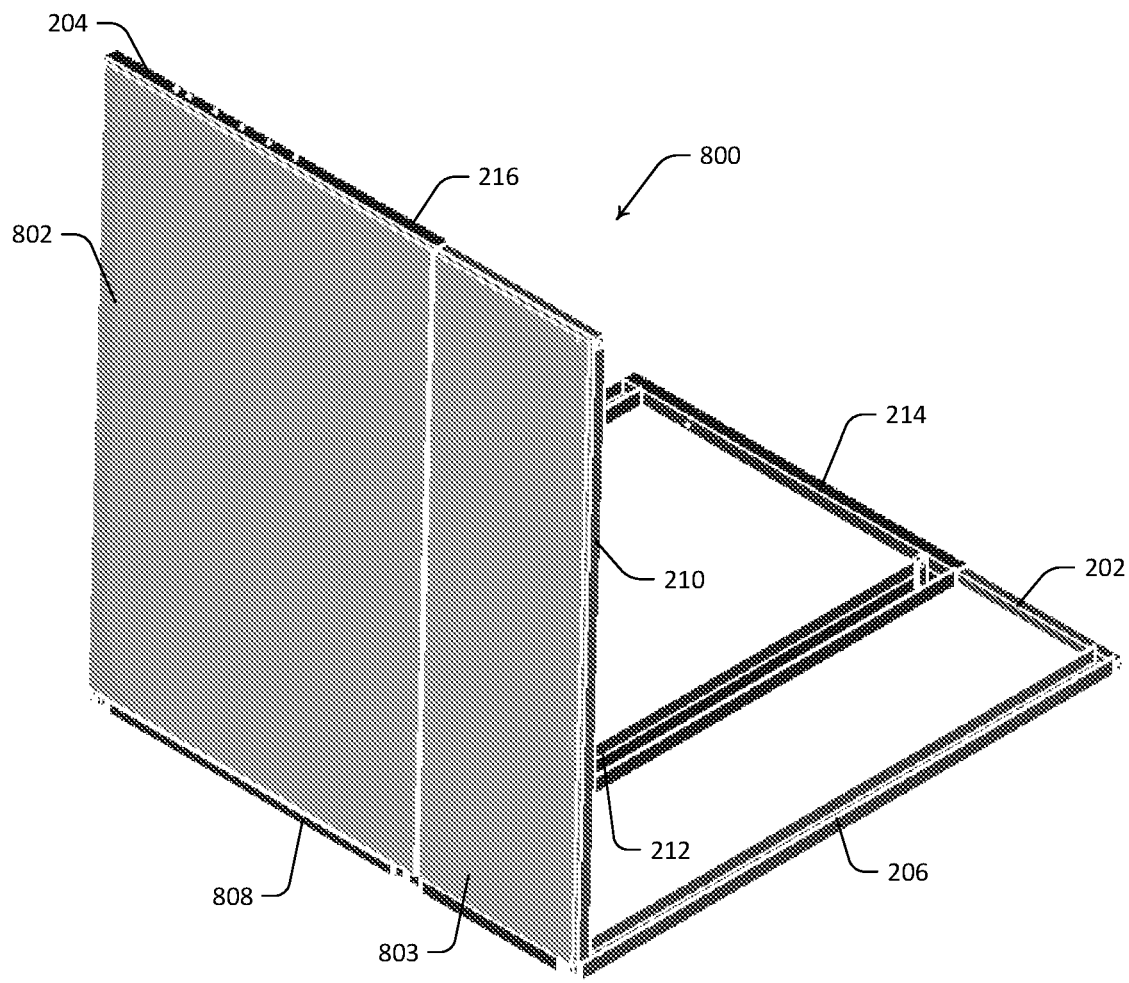
FIG. 23 is an elevated perspective view of an alternative inclinable bed apparatus having a plurality of removable support panels.
Figure 24:
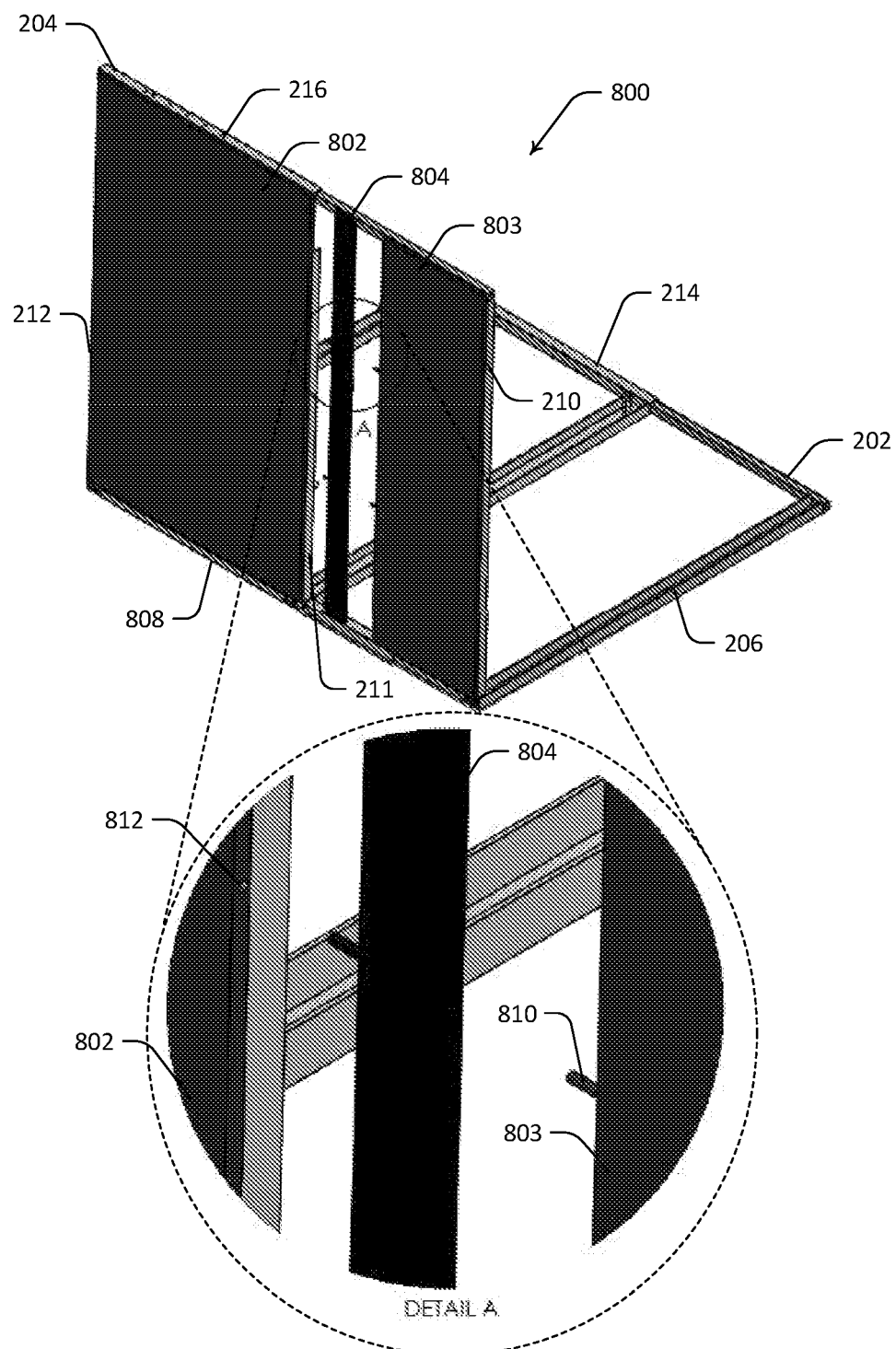
FIG. 24 is a perspective view of the inclinable bed apparatus of FIG. 23 in an expanded configuration having additional support panels installed.

Bed system 100 includes an inclinable bed apparatus 200, illustrated in FIGS. 2 to 15, which is configured to be situated on an existing bed frame 102 or mattress and provide selective inclining/reclining of a patient or user. Inclinable bed apparatus 200 is adapted to support a mattress 104 or other supportive structure for supporting a patient/user in a desired position. An alternative embodiment inclinable bed apparatus 800 is illustrated in FIGS. 23 and 24.

Bed system 100 also includes a sensor mat system 300, illustrated in FIGS. 16-20, adapted to be situated on mattress 104. Sensor mat system 300 includes a plurality of different layers as described below to sense the position and movement of a patient.

Figure 21:
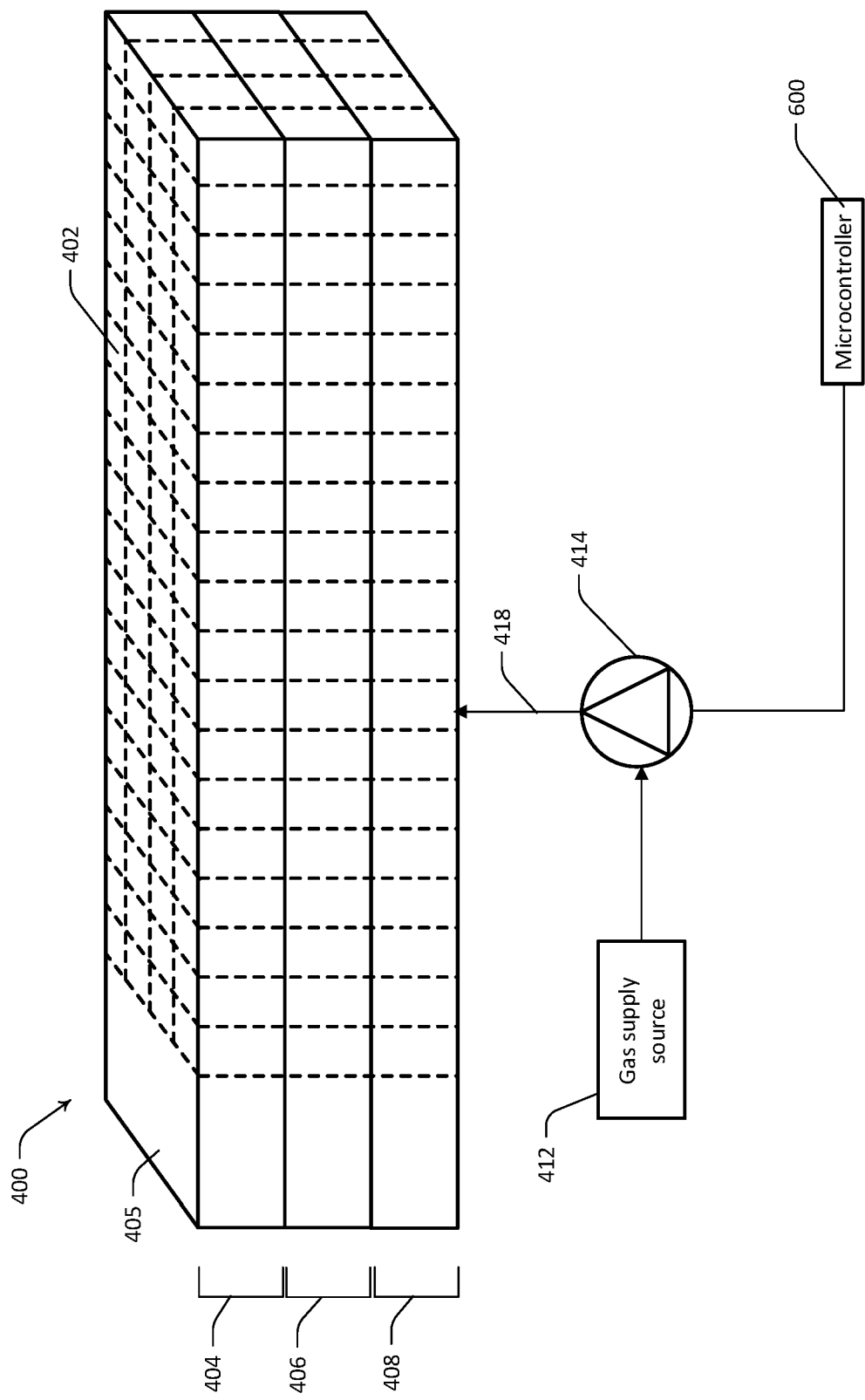
FIG. 21 is perspective view of an inflatable bladder system for use in the smart bed system of FIG. 1.
Figure 22:
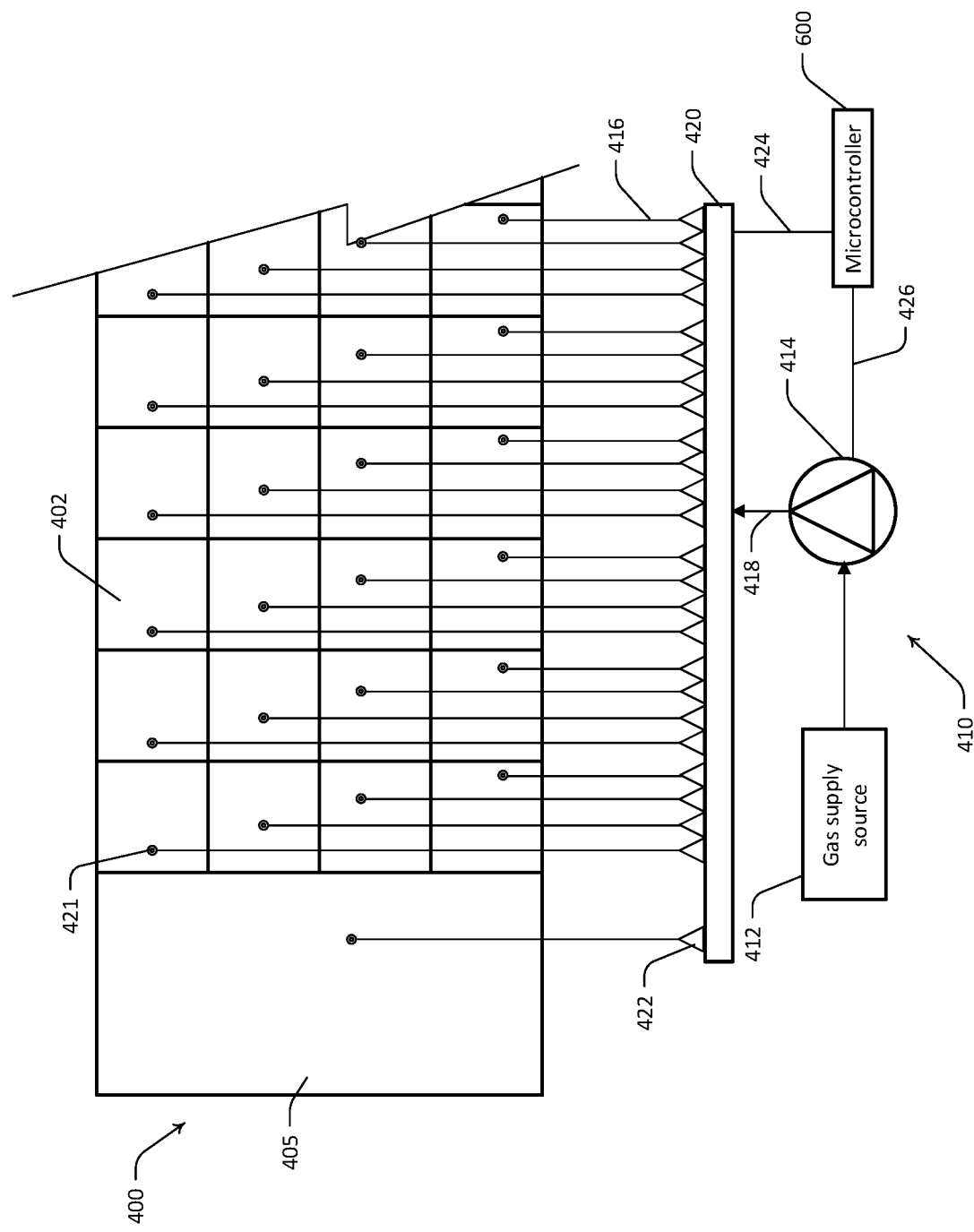
FIG. 22 is a sectional view of the inflatable bladder system of FIG. 21 illustrating a gas delivery system.

Bed system 100 further includes an inflatable bladder system 400, illustrated in FIGS. 21 and 22, having a plurality of inflatable cells for selectively adjusting the position of a patient/user or the pressure of experienced by a patient or user using bed system 100.

Figure 25:
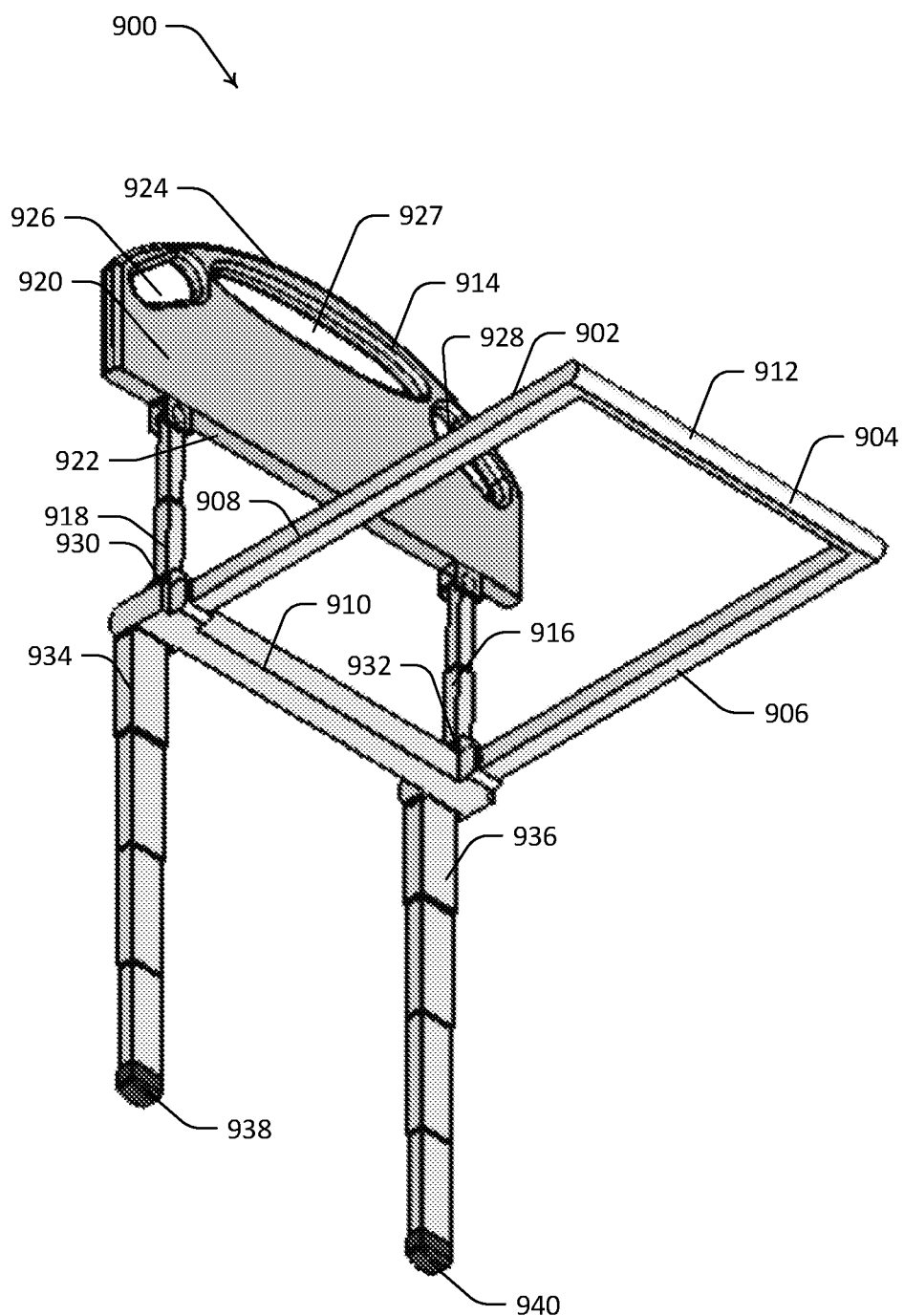
FIG. 25 is a perspective view of a support rail system for a bed.
Figure 26:
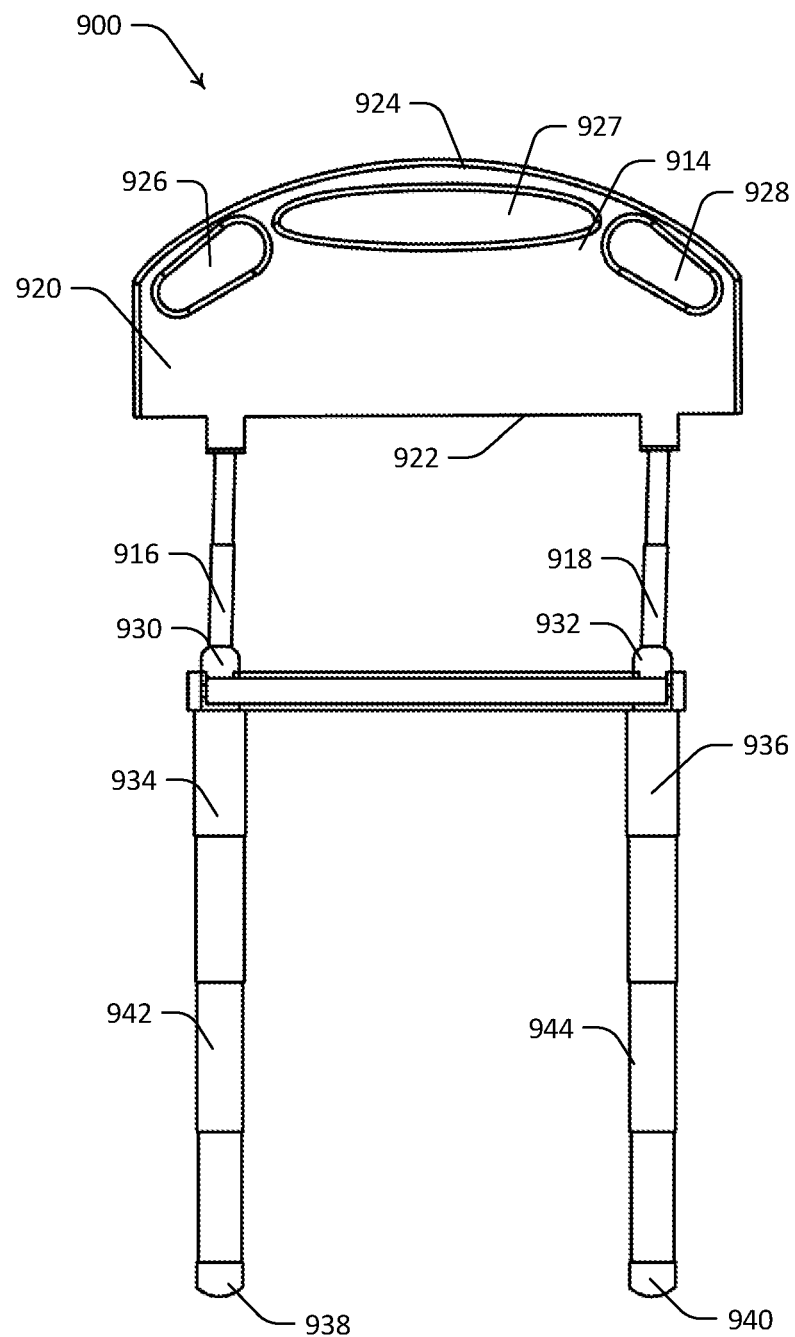
FIG. 26 is a front view of the support rail system of FIG. 25.
Figure 27:
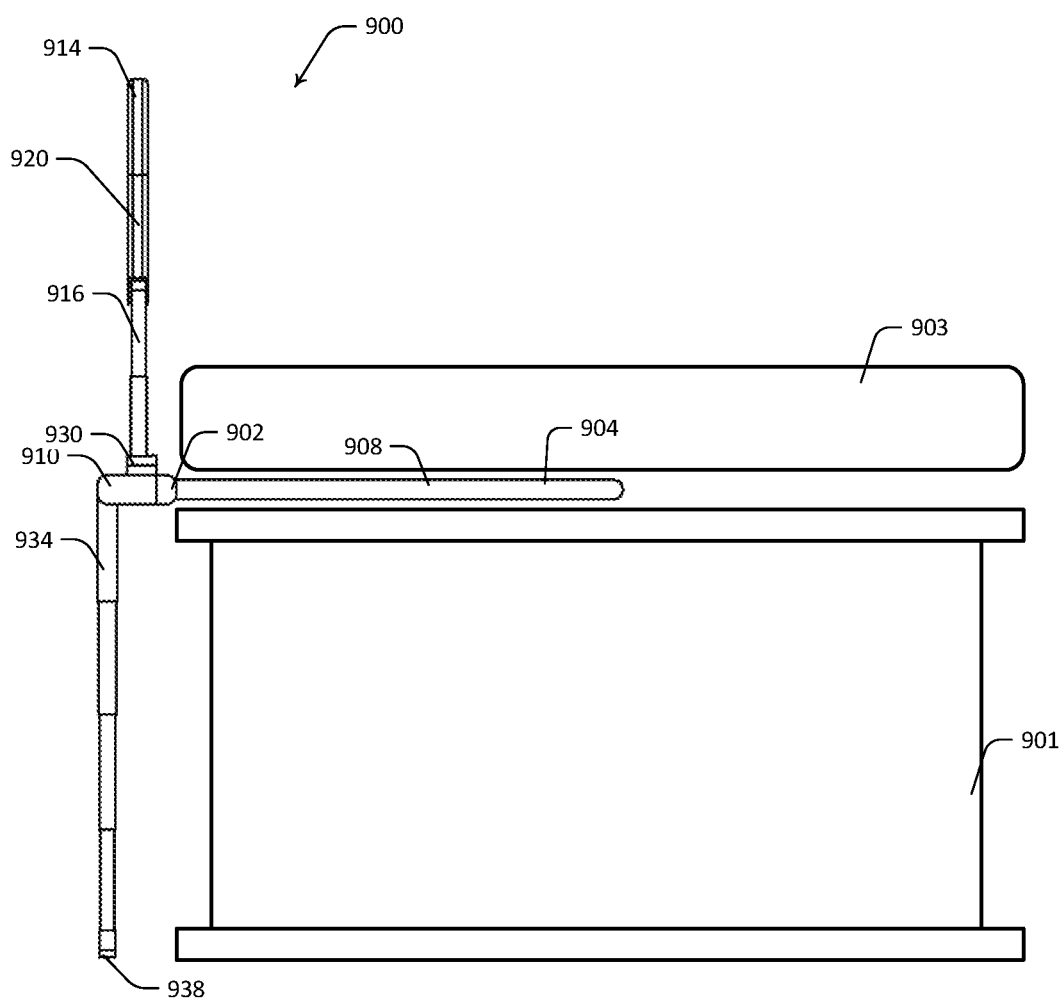
FIG. 27 is a side view of the support rail system of FIGS. 25 and 26 positioned in an operable position between a bed frame and mattress.
Figure 28:
FIG. 28 is a side view of a first example profile of the inflatable bladder system of FIGS. 22 and 23.
Figure 29:
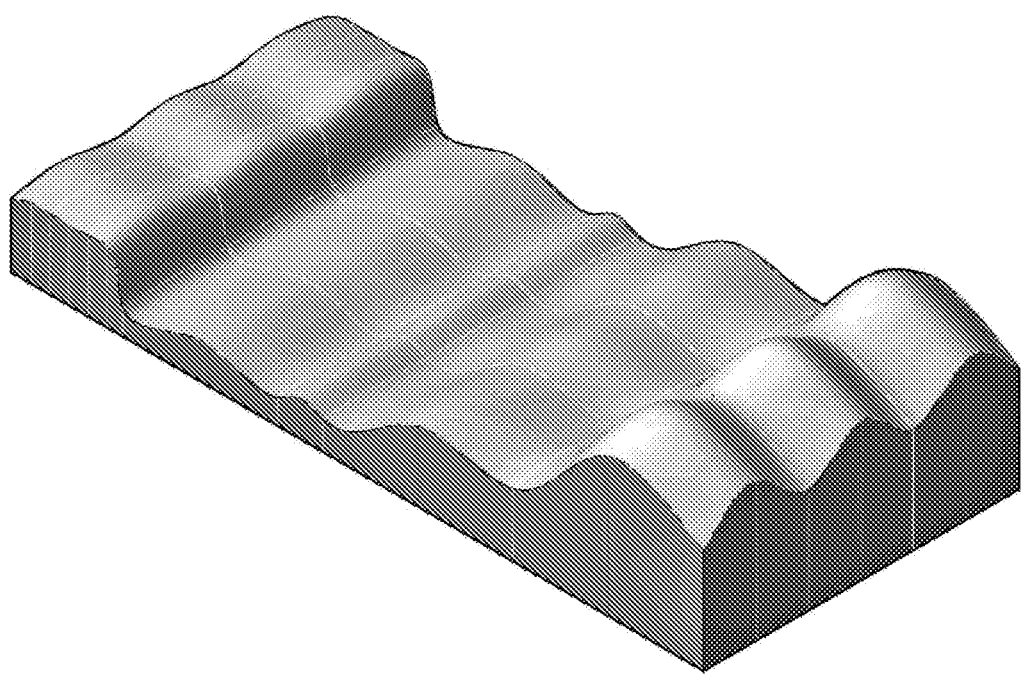
FIG. 29 is an elevated perspective view of the example profile of FIG. 28.
Figure 30:
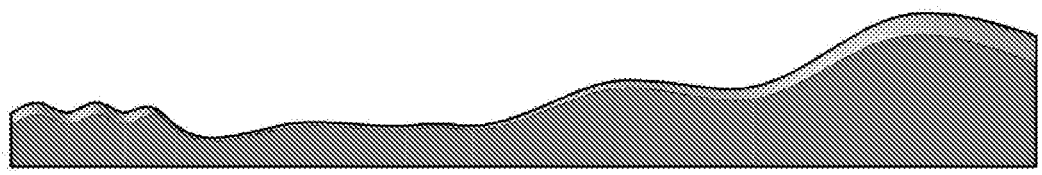
FIG. 30 is a side view of a second example profile of the inflatable bladder system of FIGS. 22 and 23.
Figure 31:
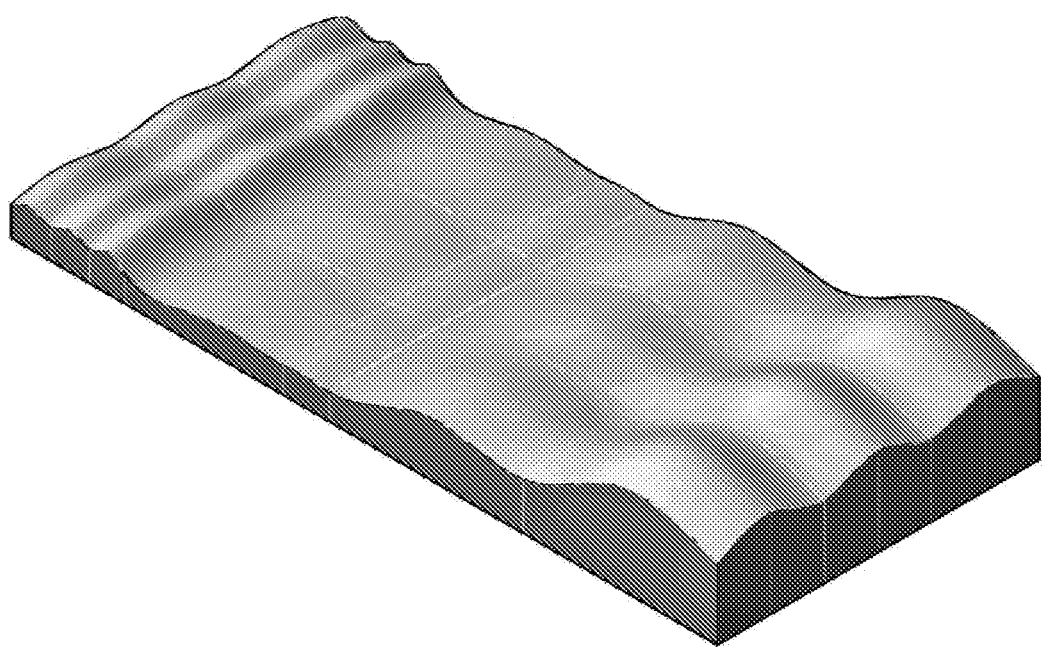
FIG. 31 is an elevated perspective view of the example profile of FIG. 30.

Bed system 100 further includes a support system 900, illustrated in FIGS. 25 to 27, for supporting a user in a bed.

Finally, system 100 includes a microcontroller 600 for performing various control and data processing operations associated with system 100, as will be described below. User input for various controls of system 100 may be provided from a remote control 700, which is in data communication with microcontroller 600.

The individual elements of bed system 100 will now be described.

Inclinable Bed Apparatus

Figure 4:
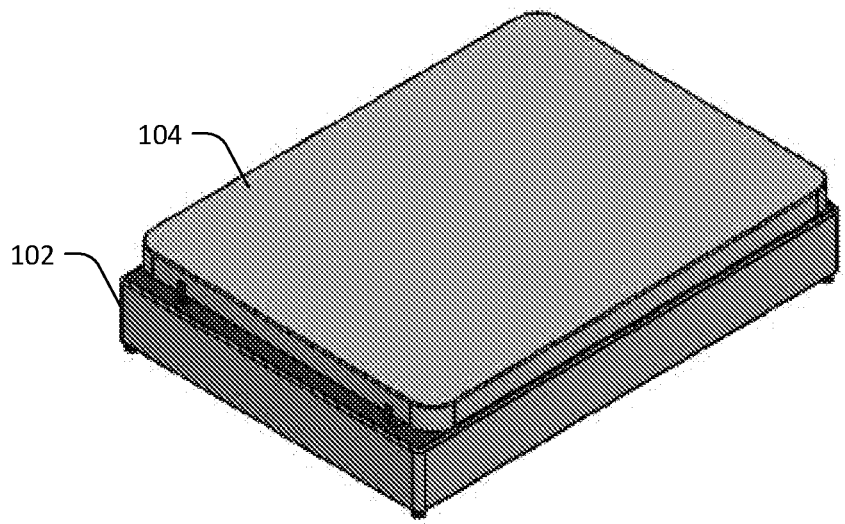
FIG. 4 is an elevated perspective view of the inclinable bed apparatus of FIGS. 2 and 3 installed in an operative position between a bed frame and a mattress.
Figure 5:
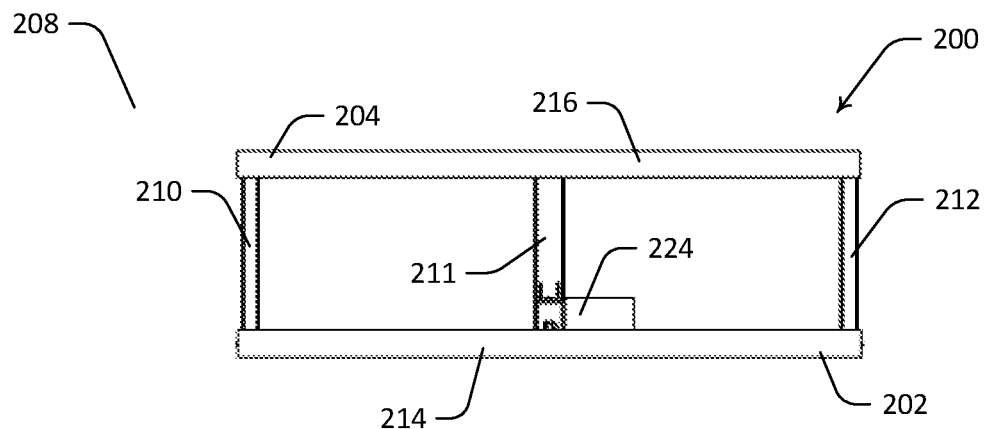
FIG. 5 is a front view of the inclinable bed apparatus of FIGS. 2 to 4 shown in a partially inclined position.

Referring to FIGS. 2 to 15, there are illustrated various views of inclinable bed apparatus 200. As illustrated best in FIGS. 2 to 4, apparatus 200 is configured to be situated on a bed frame 102 below a mattress 104. When installed in an operative position between bed frame 102 and mattress 104, apparatus 200 is largely non-visible as illustrated in FIG. 4.

Referring to FIGS. 5 to 9, apparatus 200 includes a base 202 for supportively engaging with bed frame 102 or a mattress thereof. Bed frame 102 may be a conventional bed or an adjustable bed like a hospital bed. A support arm 204 is hingedly attached to base 202 via hinged connections described below and adapted to engage a support substrate such as mattress 104 or an air bladder system described below for supporting a user. Base 202 includes three parallel disposed longitudinally extending base members 206, 207 and 208 that extend at least partially along a length of the bed frame when apparatus 200 is installed. Similarly, support arm 204 includes three parallel disposed longitudinally extending support members 210, 211 and 212. Support members 210-212 and base members 206-208 are substantially evenly spaced apart in a lateral dimension which extends across the bed frame. Support members 210-212 are located at like corresponding positions in the lateral dimension to base members 206-208.

In other embodiments, base 202 and/or support arm 204 includes at least one base member and may include a large number (e.g. 10) of longitudinally extending members in the form of slats. In one embodiment, base 202 and/or support arm 204 are formed of a single member that is substantially planar and extends laterally across at least half the width of an associated bed frame. In other embodiments, base 202 and/or support arm 204 may include a plurality angled cross members or other similar support structure.

Base 202 includes a lateral base member 214 extending laterally between base members 206-208 across a width of the bed frame. Similarly, support arm 204 includes a lateral support member 216 extending laterally between support members 210-212 across the width of the bed frame. Lateral base member 214 may be secured to longitudinally extending base members 206-208 by way of screws, bolts, spot welds, rivets or other fastening means. Similarly, lateral support member 216 may be secured to longitudinally extending support members 210-212 by way of screws, bolts, spot welds, rivets or other fastening means.

In other embodiments, base 202 and/or support arm 204 may include a plurality of laterally extending members such as rods or slats which connect with or abut the longitudinally extending members at different points.

Referring now to FIGS. 23 and 24, there is illustrated an alternative embodiment inclinable bed apparatus 800. Corresponding features of apparatus 200 are designated with like reference numerals in apparatus 800. Here support arm 204 includes a plurality of substantially planar support panels 802 to 804, which are releasably engageable with the longitudinally extending support members and lateral support member 216. In apparatus 800, an additional lateral support member 808 is included which extends between support arm 204 and base 202. Support panels 802-804 are able to be slidably inserted into C channel grooves or other guiding formations of lateral members 216 and 808, which act as a frame for panels 802-804. As best illustrated in FIG. 24, planar support panels 802-804 include engagement apertures (not shown) on one side and engagement projections (e.g. 810) on another side. The engagement apertures are positioned and configured to receive corresponding engagement projections from an adjacent support panel when slidingly engaged with each other as shown in the inset of FIG. 24. Longitudinal members 210-212 similarly include engagement apertures (e.g. 812) for slidingly engaging with the support panels 802-804.

As base 202 and support arm 204 are laterally extendible, additional support panels of different width (e.g. panel 804) may be added in a modular manner to accommodate the adjustable width of apparatus 800. It will be appreciated that the size and number of support panels may vary in different embodiments. It will also be appreciated that, in other embodiments, support panels may be engaged with lateral member 216 and 808 at spaced apart positions along their length in a similar manner to bed slats.

Support panels can be made of any rigid or semi-rigid material such as plastic (e.g. acrylic or PVA), metal or wood. In operation, support panels 802-804 provide additional support for a mattress or other support substrate laid onto apparatus 800 to better support a user.

Figure 9:
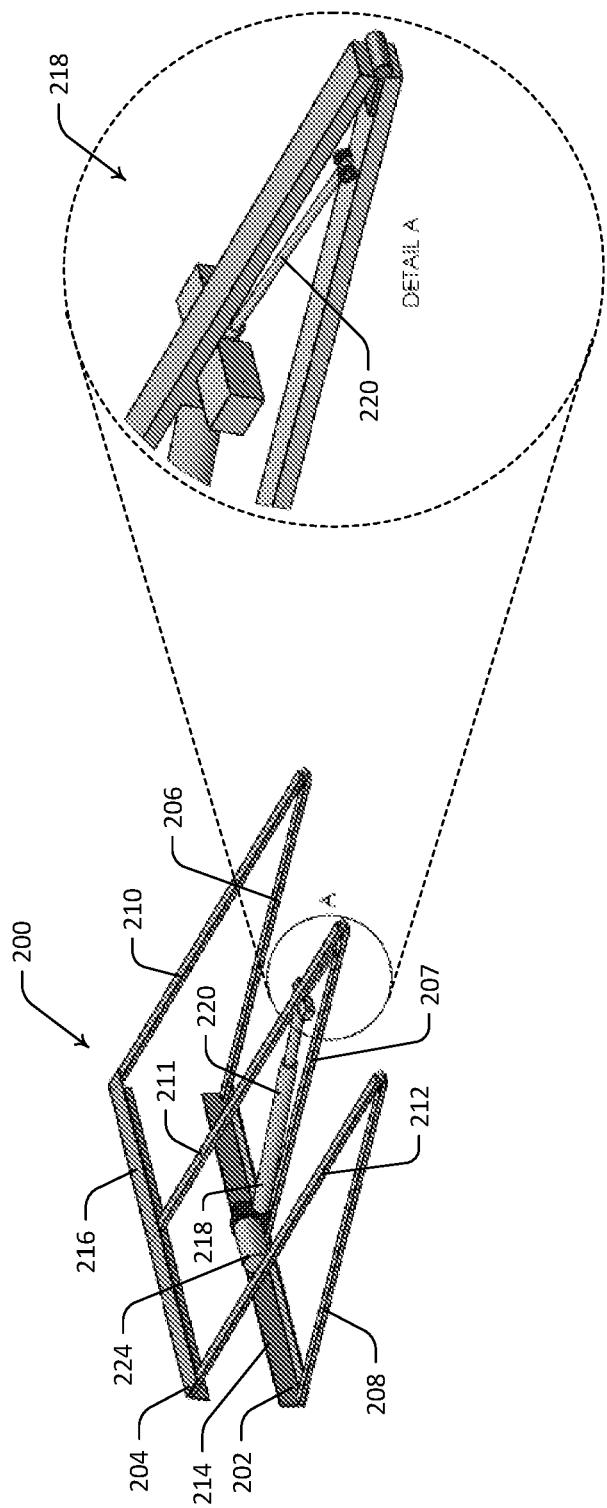
FIG. 9 is an alternative perspective view of the inclinable bed apparatus in the partially inclined position of FIGS. 5 to 8 and showing an expanded inset of an actuation system.

As best shown in FIG. 9, apparatus 200 includes an actuation system 218 that is configured to selectively rotate support arm 204 relative to base 202 between a number of predefined angular positions to support the user at different inclined angles in bed. Preferably, actuation system 218 is configured to support the user at a range of angles between 0 degrees (corresponding to a prone or supine position) and 90 degrees (corresponding to a sitting upright position). Actuation system 218 includes a hydraulic arm 220 that is mounted at one end to central base member 207 adjacent lateral base member 214 and is mechanically connected at its other end to central support member 211 adjacent a hinge joint 222 connecting support member 211 with base member 207. Hydraulic arm 220 includes a telescopic member that is selectively adjustable in length to angularly incline support arm 204 relative to base 202.

Figure 10:
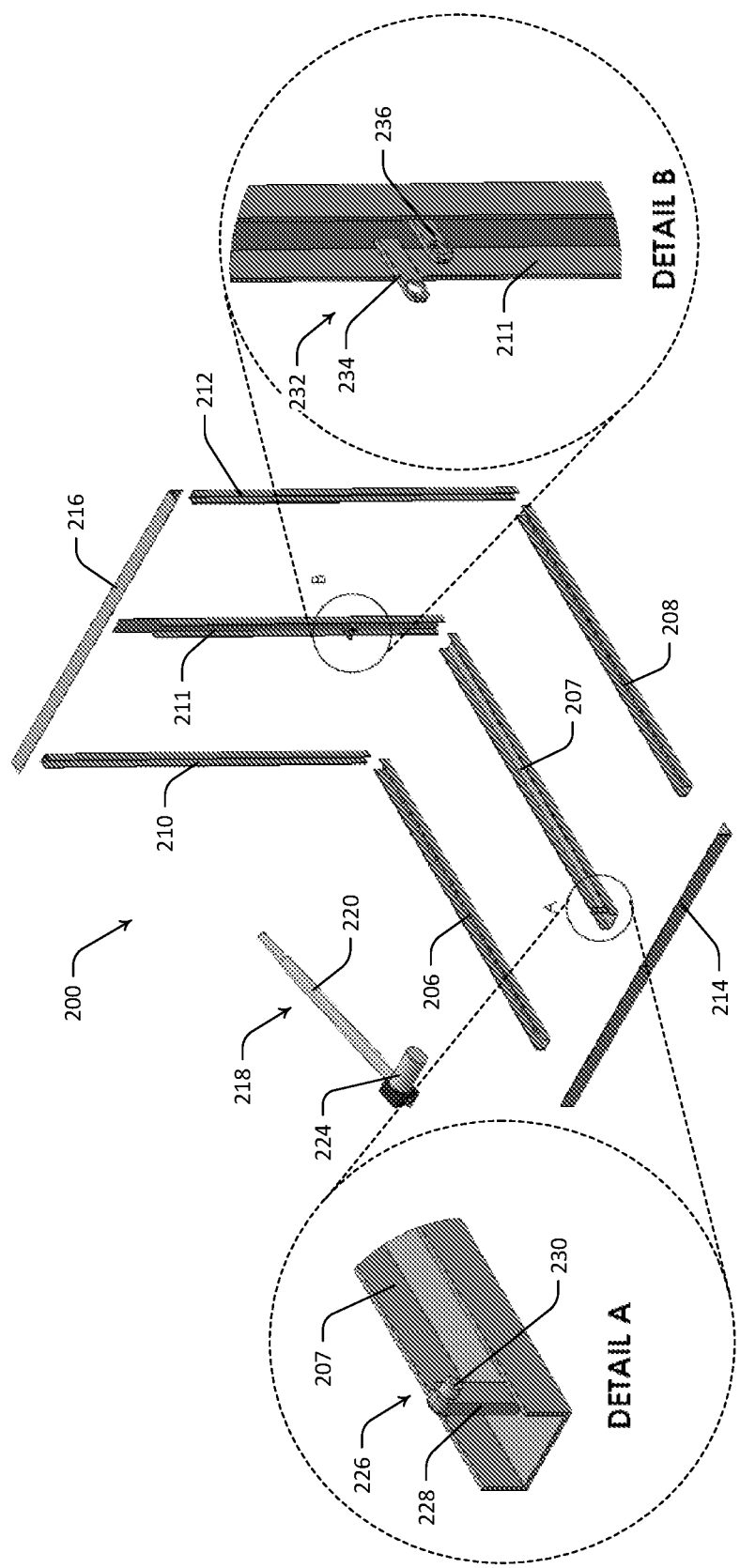
FIG. 10 is an exploded view of the inclinable bed apparatus with insets showing connections of an actuation system.

Hydraulic arm 220 is mounted to base member 207 and support member 211 by hinge mechanisms as illustrated in FIG. 10. Hydraulic arm 220 is mounted to base member 207 by hinge mechanism 226 having a projecting flange 228 with corresponding aperture for receiving a locking screw 230. Screw 230 projects through flange 228 and into a corresponding aperture (not shown) on hydraulic arm 220 to rotatably secure hydraulic arm 220 to base member 207 using a locking nut (not shown). Hydraulic arm 220 is similarly mounted to support member 211 by hinge mechanism 232 having a pair of like flanges 234 and 236. Each flange includes a corresponding aperture for receiving a locking screw (not shown) to rotatably secure hydraulic arm 220 to support member 211 using a locking nut (not shown). When secured in place, an end 238 of hydraulic arm 220 abuts an inner surface of support member 211 and provides sufficient force to maintain support arm 204 in a desired inclined position.

In alternative embodiments, hydraulic arm 220 may be mounted to base member 214 and support member 211 by way of conventional fastening means such as screws, bolts, spot welds or rivets.

FIG. 10 also illustrates one preferred form of the various members used to form base 202 and support arm 204. In particular, longitudinal members 206-208 and 210-212 are formed from C-section channel members and lateral members 214 and 216 are formed of L-shaped members. Each of the members are preferably formed of a rigid but lightweight material such as aluminium alloy 6060. This is a medium strength heat treatable alloy that is light in weight. The C-section channel design provides the longitudinal members (which are the primary weight bearing members) with extra strength to hold larger weight, whilst reducing the weight of the device itself in total. In other embodiments, more premium models may use more expensive materials such as titanium, steel or carbon fibre. Furthermore, in some embodiments, the various members may be formed of more solid structures such as members having a square cross-sectional area.

Figure 6:
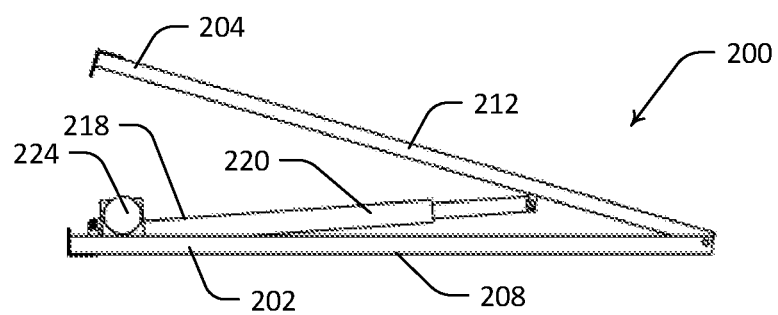
FIG. 6 is a side view of the inclinable bed apparatus in the partially inclined position of FIG. 5.
Figure 7:
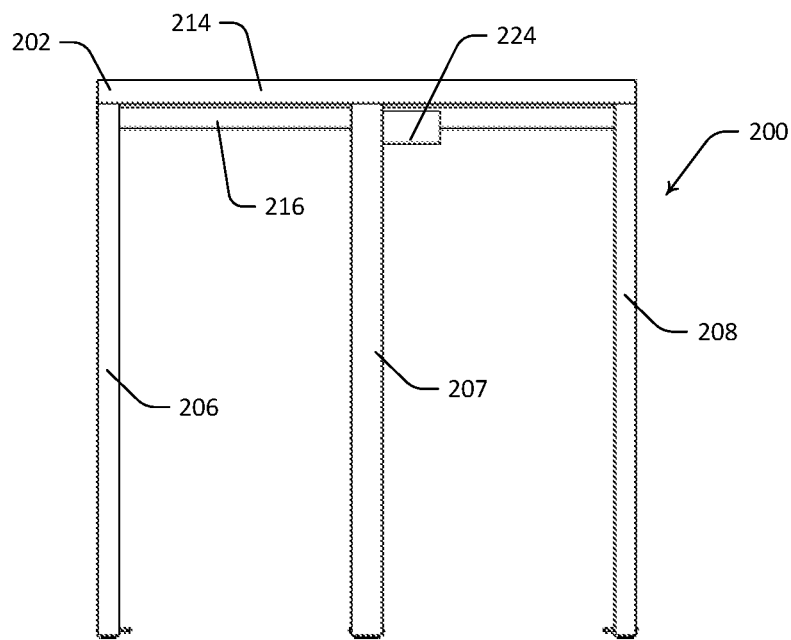
FIG. 7 is an underside view of the inclinable bed apparatus in the partially inclined position of FIGS. 5 and 6.
Figure 8:
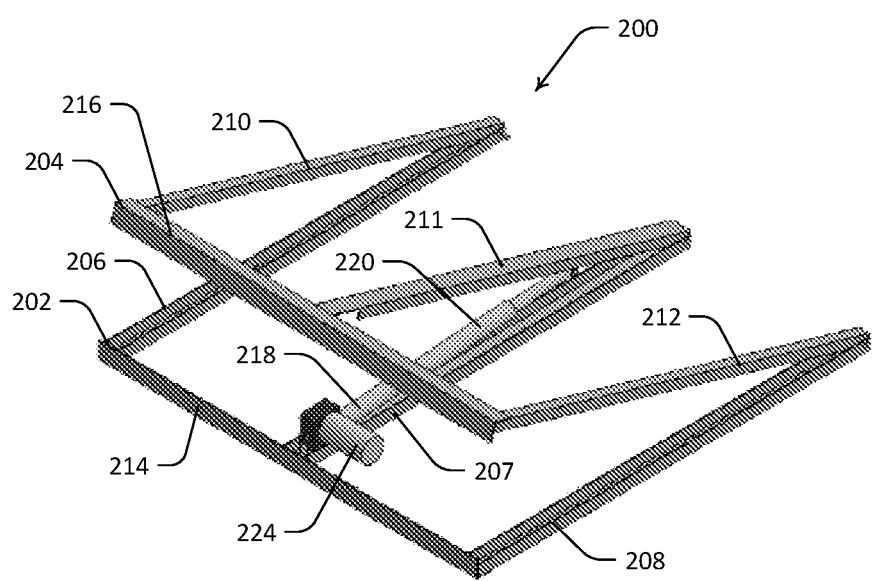
FIG. 8 is an elevated perspective view of the inclinable bed apparatus in the partially inclined position of FIGS. 5 to 7.

As best shown in FIGS. 6, 8 and 9, actuation system 218 also includes an electric linear actuator 224 configured to linearly extend or retract hydraulic arm 220 in response to an actuation signal provided from an associated microcontroller 600 (see FIG. 1). The actuation signal may include one of a series of voltage signals which causes linear actuator 224 to move hydraulic arm 220 between a number of predefined positions to incline support arm 204 at one of a plurality of angular positions relative to base 202. The stroke length of linear actuator 224 is designed to lift users to a maximum height of 90 degrees. A 90-degree inclination is particularly important as it allows users who have had strokes to eat without choking.

In some embodiments, actuator system 218 includes an automatic strength spring (not shown), which attaches behind linear actuator 224. This spring acts to both control the release of linear actuator 224 in case of an emergency power shutdown, and to minimize force by transferring the leverage of the device into movement more efficiently. In other embodiments, different types of electromechanical actuators may be used in place of linear actuator 224.

Figure 11:
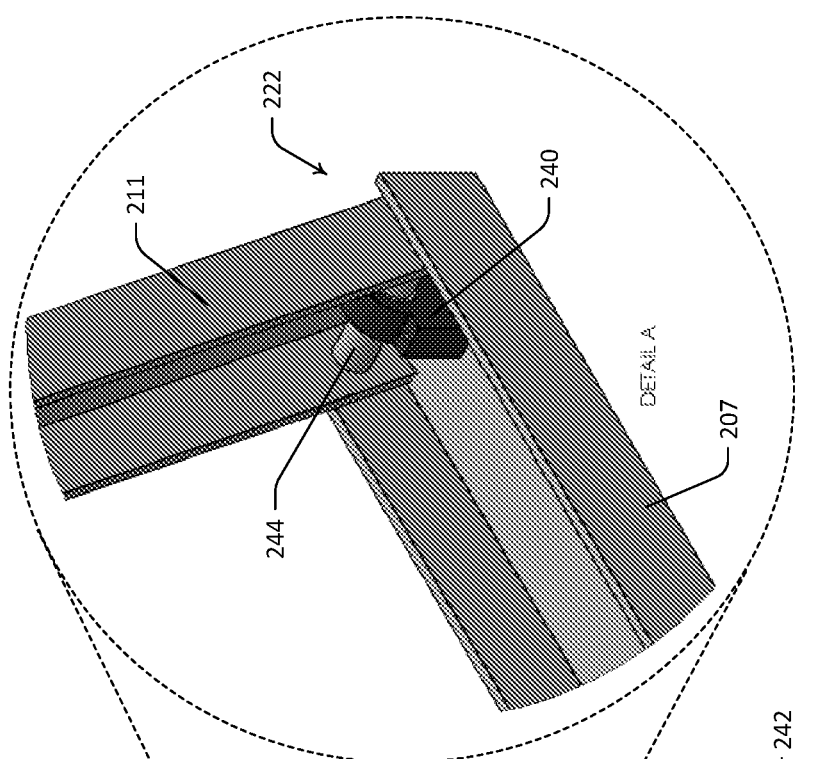
FIG. 11 is an elevated perspective view of the inclinable bed apparatus in an almost fully inclined position and showing an expanded inset of a hinge joint.
Figure 11:
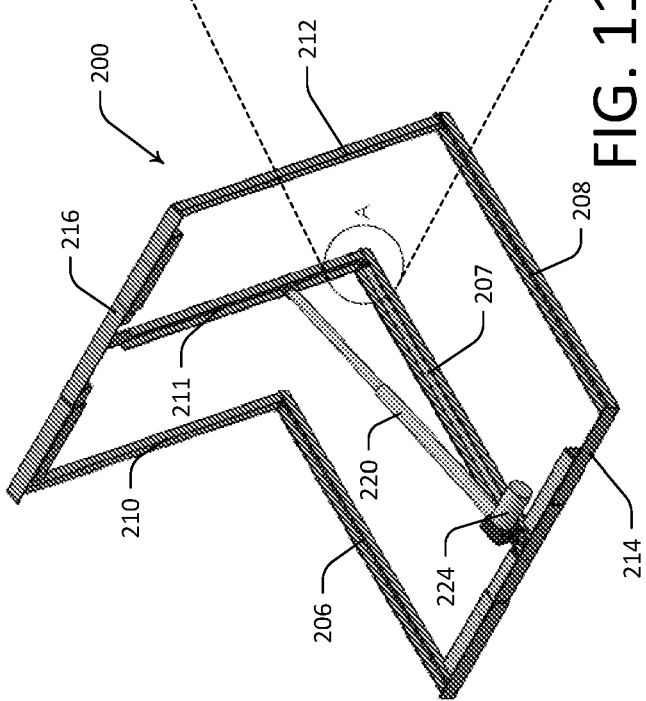
Figure 12B:
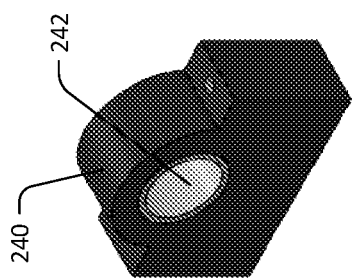
FIG. 12B is a perspective view of the bearing of FIG. 12A.
Figure 12A:
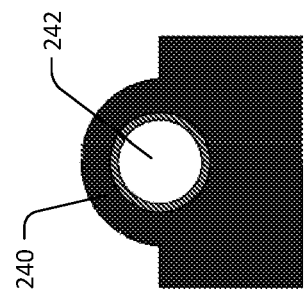
FIG. 12A is a front view of a bearing of the hinge joint illustrated in FIG. 11.

Referring now to FIGS. 11 and 12, hinge joint 222 is illustrated in more detail. Hinge joint includes a bearing 240 having a substantially circular aperture 242 for receiving a corresponding hinge pin 244 that extends between the C-section channel of support member 211. Bearing 240 is mounted inside the C-section channel of base member 207 as shown in the inset of FIG. 11 and transfers, in part, the weight of support member 211 and associated load on support arm 204 while facilitating rotational motion of support member 211. Similar hinge joints are located between base member 206 and support member 210 and between base member 208 and support member 212.

Figure 13:
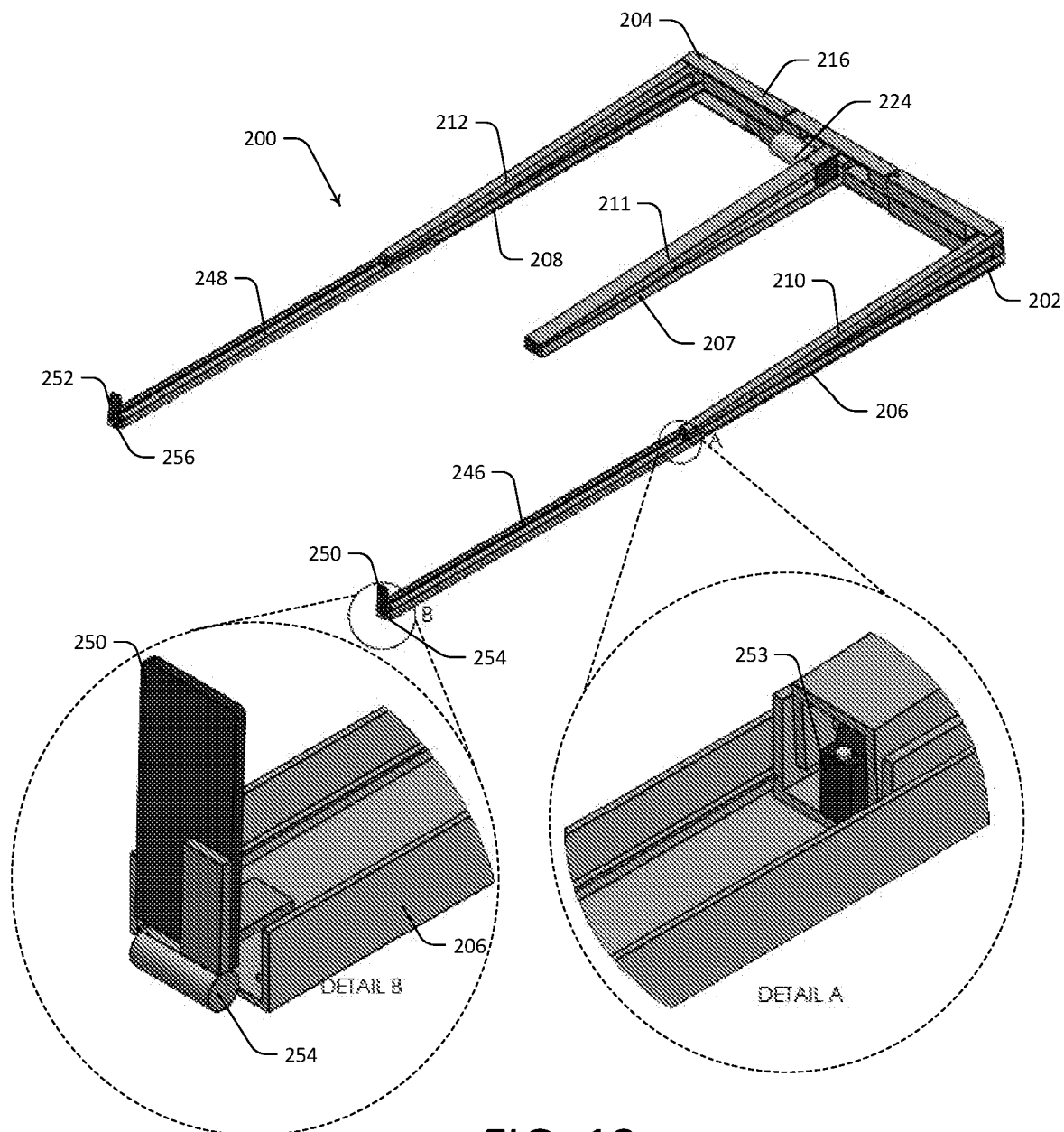
FIG. 13 is an elevated perspective view of the inclinable bed apparatus showing retractable arms in an extended position extending from base members.

Referring now to FIG. 13, to accommodate different length mattresses (or other support substrates), base members 206 and 208 are longitudinally adjustable in length and include respective extension arms 246 and 248. Extension arms 246 and 248 extend telescopically along the length of members 206 and 208 in a direction towards a foot of the bed frame. In other embodiments, base member 207 is also telescopically extendible in length.

As shown in inset A of FIG. 13, extension arms 246 and 248 include a similar C-section channel structure but have a slightly wider channel, thereby being able to telescopically sleeve around base members 206 and 208. An internal locking mechanism 253 allows for actuation of a downwardly extending locking pin (not shown) into one of a plurality of longitudinally spaced locking apertures (not shown) in extension arm 246 to lock arm 246 in a particular longitudinal position. A similar locking mechanism is present in extension arm 248. In other embodiments, locking mechanism 253 includes a spring lock or other type of locking device.

As shown in inset B of FIG. 13, extension arms 246 and 248 include upwardly rotatable feet 250 and 252 to abut an end of a mattress (or other support substrate). Feet 250 and 252 are rotatable about respective hinge joints 254 and 256 between a retracted position within the channel of base members 206 and 208 and a vertical operative position illustrated in FIG. 13. In the operative position, feet 250 and 252 serve as longitudinal abutments for supporting a mattress (or other support substrate) on support arm 204 of apparatus 200.

Figure 14:
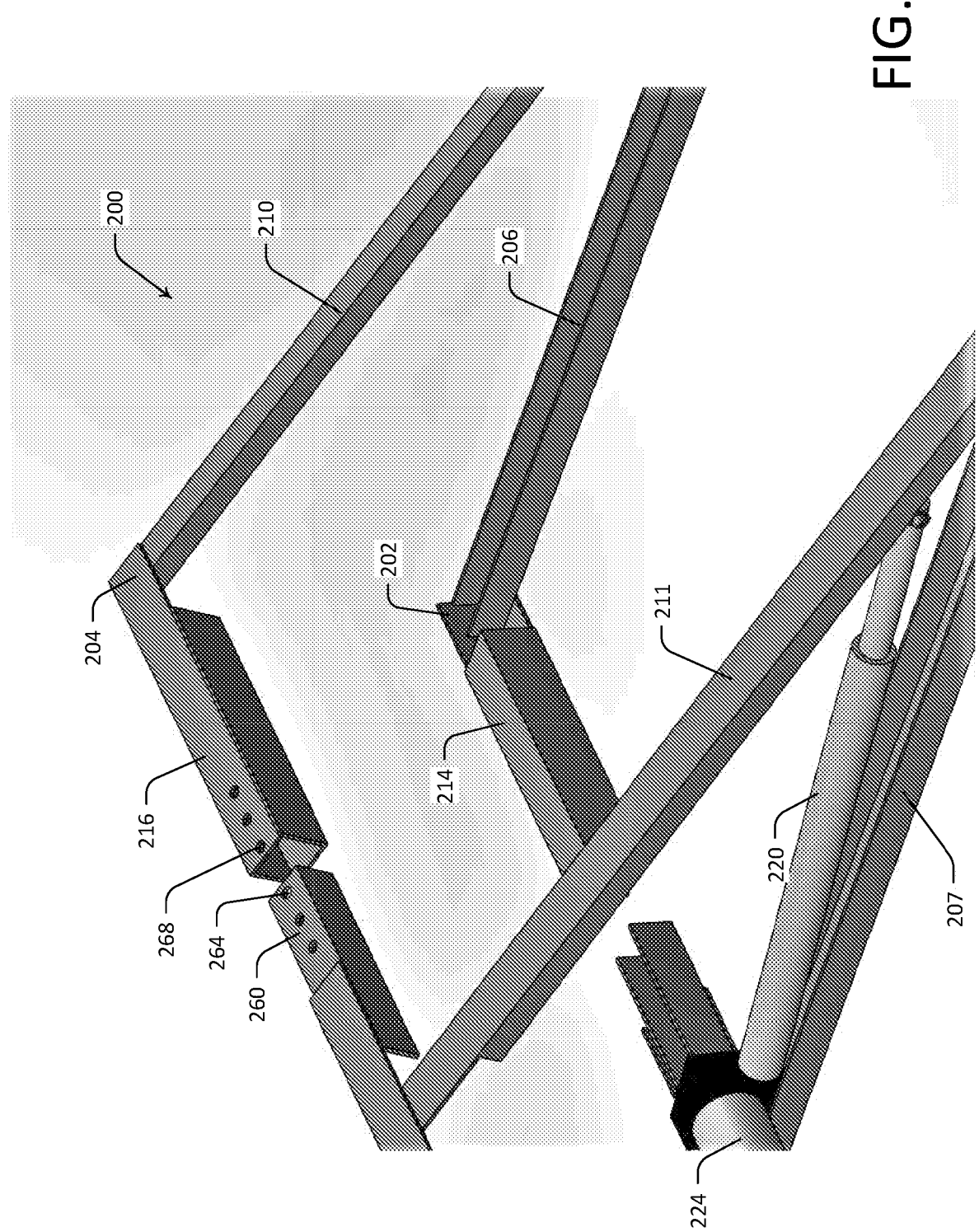
FIG. 14 is a perspective view of the inclinable bed apparatus illustrating lateral adjustability of lateral base and support members to adjust a width of the apparatus.
Figure 15:
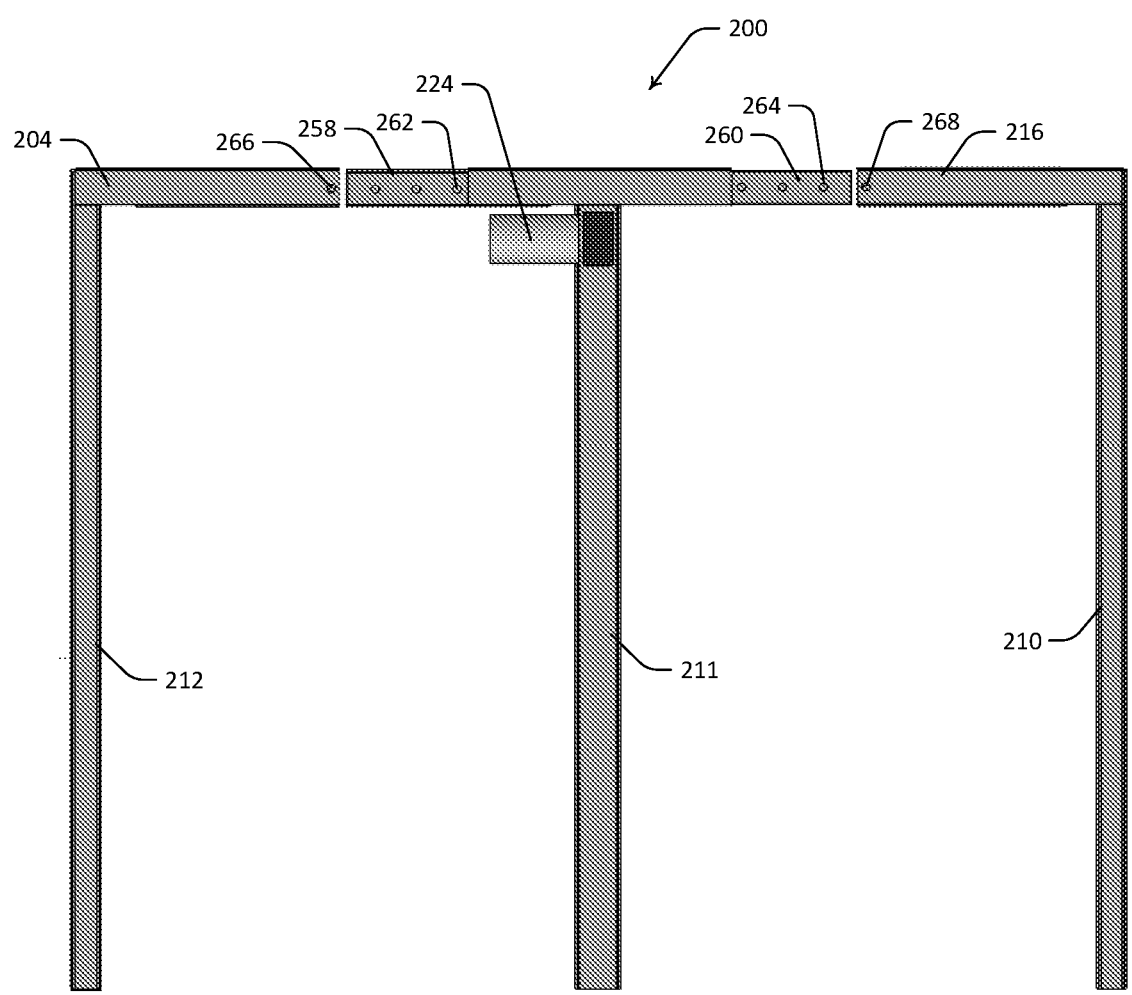
FIG. 15 is a plan view of the inclinable bed apparatus illustrating lateral adjustability of lateral base and support members to adjust a width of the apparatus.

Referring now to FIGS. 14 and 15, to accommodate different width mattresses (or other support substrates), lateral base member 214 and lateral support member 216 are laterally telescopically adjustable in length. In particular, lateral support member 216 includes intermediate sections 258, 260 formed of a C-section channel structure and being adapted to laterally slide within the L-shaped structures of member 216 to adjust an overall width of lateral support member 216. As illustrated, intermediate sections 258 and 260 include a plurality of longitudinally spaced apertures (e.g. 262 and 264) which may be aligned with corresponding apertures (e.g. 266 and 268) of the remaining sections of lateral support member 216 and adapted to receive respective locking pins (not shown) to lock the sections in place in a fixed width. Similar adjustment is provided to lateral base member 202, which has similar intermediate sections and apertures (not shown).

The inclinable bed apparatus 200 described above is able to be stored in a compact configuration with feet 250 and 252 rotated into their retracted position, extension arms sleeved within corresponding base members 206 and 208, lateral support and base members retracted laterally into their smallest position and support arm 204 reclined against base 202. In this position, the spatial footprint of apparatus 200 is quite small and may be stored under a bed or within a closet.

Figure 2:
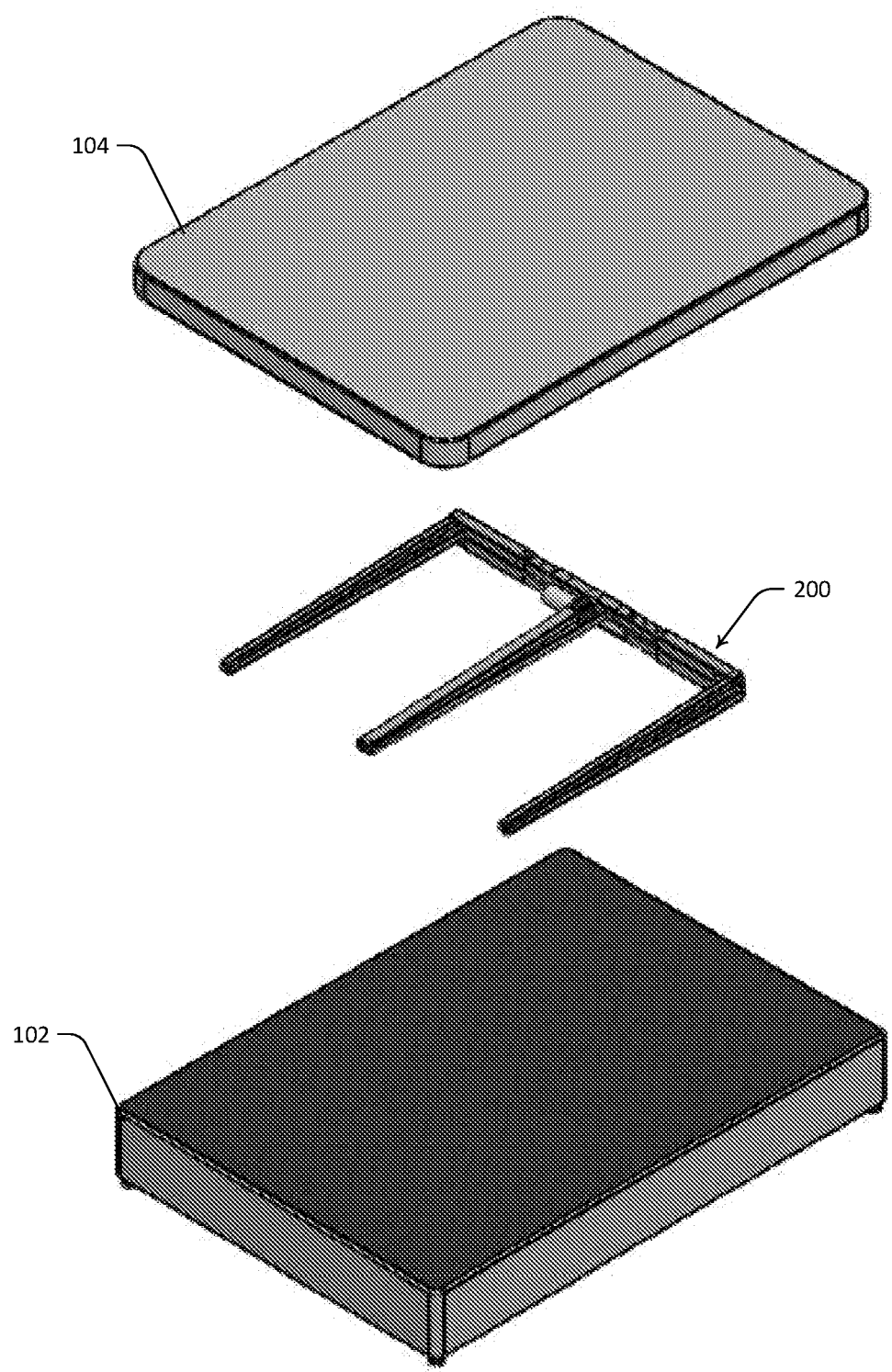
FIG. 2 is an exploded perspective view of a bed having an inclinable bed apparatus located between a bed frame and mattress.
Figure 3:
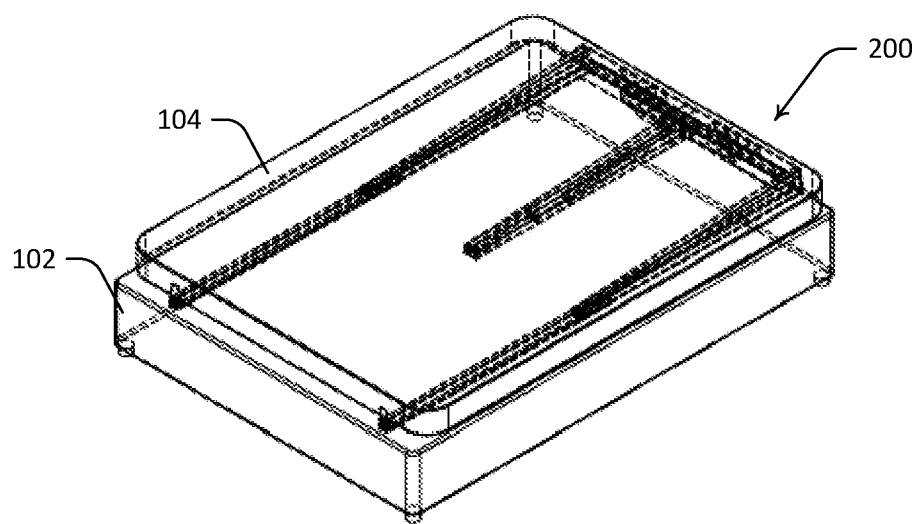
FIG. 3 is an elevated perspective window view of the inclinable bed apparatus of FIG. 2 installed in an operative position between a bed frame and a mattress.

To use apparatus 200, it is first placed on a bed frame or mattress of an existing conventional bed (either on top of the mattress or beneath it as illustrated in FIG. 2). Lateral base member 214 and lateral support member 216 are then adjusted in lateral length (as shown in FIGS. 14 and 15) and locked in place to fit the width of the existing bed frame or mattress. With the lateral members locked in place, extension arms 246 and 248 may be slidingly extended from base members 206 and 208, locked and feet 250 and 252 rotated upwards into the operative position. A support substrate such as a mattress or inflatable bladder system (described below) or combination thereof is then able to be placed on top of apparatus 200. Feet 250 and 252 support the mattress or substrate from sliding longitudinally.

Additional engagement apparatus may also be included to securely support apparatus 200 to the bed frame. In one embodiment, one or more adjustable or elastic straps are engageable with base 202 and/or the bed frame to secure apparatus 200 to the bed frame. Preferably, a multiple-strap system is provided which attaches the apparatus to any bed frame at numerous points to maximise transference of force. The straps are preferably formed of a soft fabric material to minimize discomfort to patients. Similarly, engagement apparatus such as straps may be used to secure a mattress or support substrate onto apparatus 200.

In another embodiment, overlaying sheets having elastic outlays, with Velcro or other materials may be used to attach the sheet down onto apparatus 200 with appropriate tabs and hooks attached to base 202. Such a sheet will not only secure apparatus 200 to the bed frame, but will make changing sheets an easy procedure.

In a further embodiment, a mattress-adhesive hook may be provided which connects apparatus 200 to a mattress positioned thereon. In a further embodiment, a custom mattress may be produced which attaches to apparatus 200 via in-built hooks.

In operation with a conventional bed, apparatus 200 can convert the conventional bed into an affordable alternative to an expensive hospital bed. In conjunction with the additional elements described below, apparatus 200 can operate as a smart bed system to at least partially address the problems described above. For example, apparatus 200 can make it easy for disabled patients to move around.

Linear actuator 224 is able to be controlled via microcontroller 600 to allow a user (e.g. doctor, clinician or patient) to control the angle of incline of support arm 204. User input may be provided by electrical or wireless signals from remote control 700 or control panel, or from voice commands received by a microphone and processed by microcontroller 600. For example, the user may be able to provide audible commands like "bed up", "bed down", "bed fully up", "bed fully down" and "stop". Microcontroller 600 may also allow for voice recognition to identify specific users for security purposes. In some embodiments, microcontroller 600 is in wireless communication (via Bluetooth, Wi-Fi or the like) with a user/patient's smartphone and user input can be provided via a software application to control apparatus 200.

Microcontroller 600 may further be able to provide control signals to linear actuator 224 from inputs gained from sensors of a sensor system described below. Microprocessor 600 may include a communications device for collecting various data from remote devices or an associated sensor system and provide an API, from which inputs can be provided to linear actuator 224. The communications device may facilitate data communication by one or more of Bluetooth, infrared, Wi-Fi, Li-Fi, and various other communications protocols, as well as via direct connection to apparatus 200.

Microcontroller 600 may also integrate with an associated data or telephone network to enable voice calls to healthcare staff and other parties. Microcontroller 600 can also act as a relay point at the patient end to connect to healthcare workers or third parties such as family members. This allows other parties such as family members to monitor patient status via a phone, tablet, personal computer, or other device using a dedicated software application.

Microcontroller 600 and linear actuator 224 are powered by an electrical connection (not shown) to a mains power source and/or a battery module.

Further functionality of microcontroller 600 is described below.

In some embodiments, linear actuator 224 may be manually overridden and support arm 204 manually inclined by way of a ratchet-crank, or pulley system. This will allow for manual intervention when not connected to electricity (e.g. during a blackout) or when the battery is depleted. A manual CPR override may be provided which releases all electronic control to place the user in a prone position.

As will be described, inclinable bed apparatus 200 is operable in conjunction with sensor mat system 300, inflatable bladder system 400 and microcontroller 600 to provide smart bed system 100.

Patient Sensor System

Referring now to FIGS. 16 to 20, there is illustrated a sensor mat system 300 for use in sensing a user's position and motion in a bed. Sensor mat system 300 is adapted to be positioned directly underneath a user or under a mattress or other support substrate such as the inflatable bladder system described below. Sensor mat system 300 may be disposed onto support arm 204 of apparatus 200 described above.

Figure 16:
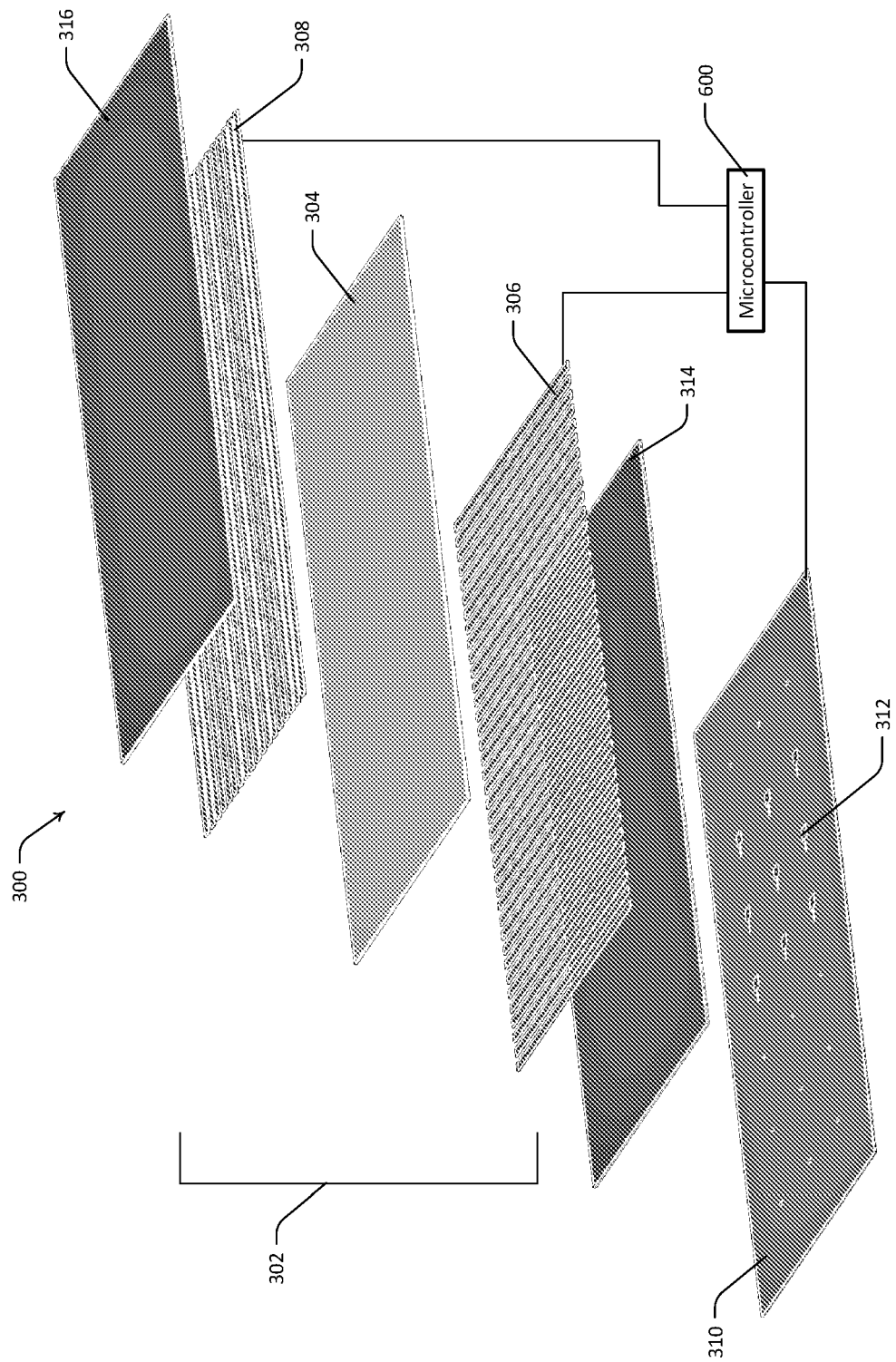
FIG. 16 is an exploded view of a sensor mat system for use in the smart bed system of FIG. 1.
Figure 18:
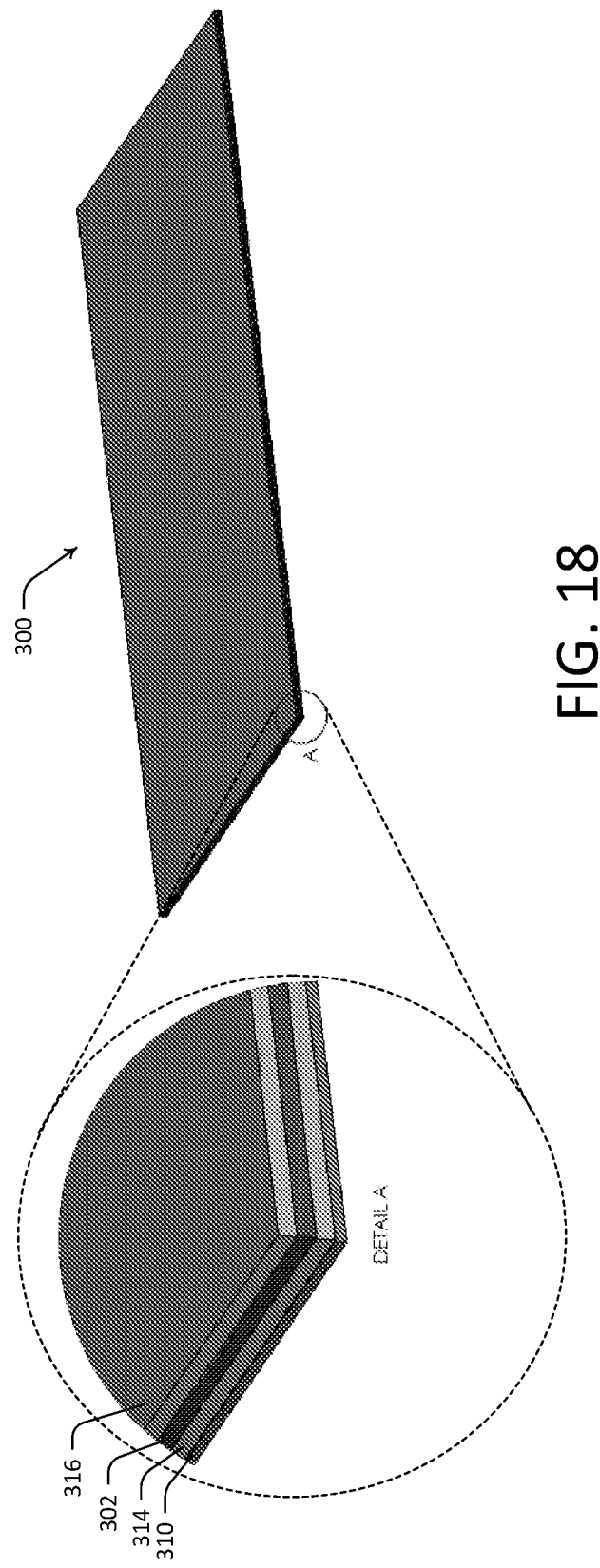
FIG. 18 is an elevated side perspective view of the sensor mat system of FIGS. 16 and 17 illustrating different layers of the system.

As illustrated in FIG. 16, sensor mat system 300 includes a piezoelectric sensing layer 302, including a piezoelectric material 304 surrounded by a plurality of electrically conductive elements 306 and 308. Piezoelectric sensing layer 302 is formed of three individual sub-layers—the piezoelectric material 304 and the upper and lower electrically conductive elements 306 and 308. In operation, these three sub-layers are adhered together to form a single layer as illustrated in FIG. 18. Piezoelectric sensing layer 302 is configured to generate first pressure signals in response to an applied pressure by the user laying on sensor mat system 300.

System 300 also includes a pressure sensor layer 310 including a plurality of spatially distributed sensors (e.g. 312) configured to generate second pressure signals in response to the applied force. These sensors may be one or more of force sensitive resistors, strain gauges, load cells, capacitive transducers and/or stretch sensors, which are designed to provide positional inputs in strategic locations, and also to calibrate the above piezoelectric layer. Additional sensors may be embedded within sensor layer 310, such as one or more of thermometers, ultraviolet (UV) light detectors.

As illustrated in FIG. 16, system 300 also includes a sensor microcontroller 600 in electrical communication with the electrically conductive elements 306 and 308 and the sensors 312 via electrical wiring. In alternative embodiments, electrically conductive elements 306 and 308, and sensors 312 are able to communicate with microcontroller 600 wirelessly.

Microcontroller 600 is configured to receive and process the first and second pressure signals to generate pressure data indicative of a spatial distribution of pressure across the sensor mat. In particular, microcontroller 600 is configured to determine a position and movement patterns of a subject laying on the sensor mat system based on the pressure data. Preferably, microcontroller 600 is capable of generating pressure data as a function of time to perform time dependent and historical analysis such as patient movement patterns. Based on this, further advanced analysis can be performed, which is described below.

Although microcontroller 600 is described as being the same as that described above in relation to apparatus 200, it will be appreciated that, in some embodiments, separate microcontrollers are used for different elements of smart bed system 100. In some embodiments, a separate computer device may serve in place of microcontroller 600.

System 300 also includes a gel layer 314 disposed between piezoelectric sensing layer 302 and pressure sensor layer 310 and a further gel layer 316 disposed above conductive element 308 (adjacent the separate mattress or support substrate). These gel layers allow for increased transfer and distribution of weight (and therefore stretch) to be transferred onto the sensors, as well as to increase user comfort. Gel layer 314 can also be used to shift the location of pressure sensor layer 310 which may be concentrated around areas of high requirement (e.g. ilium/hip bone in pressure sore areas).

Figure 17:
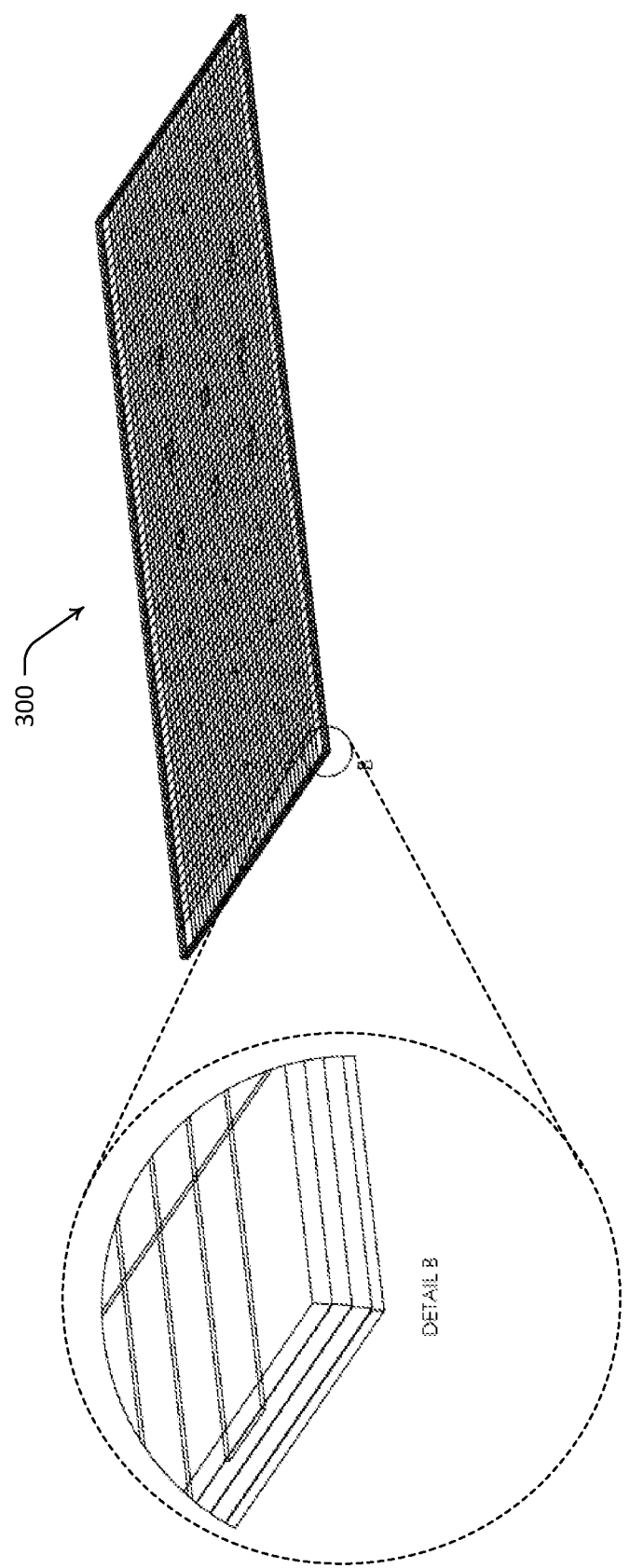
FIG. 17 is a cutaway view of the sensor mat system of FIG. 16 illustrating a grid structure of electrically conductive elements extending across a piezoelectric material layer.
Figure 19:
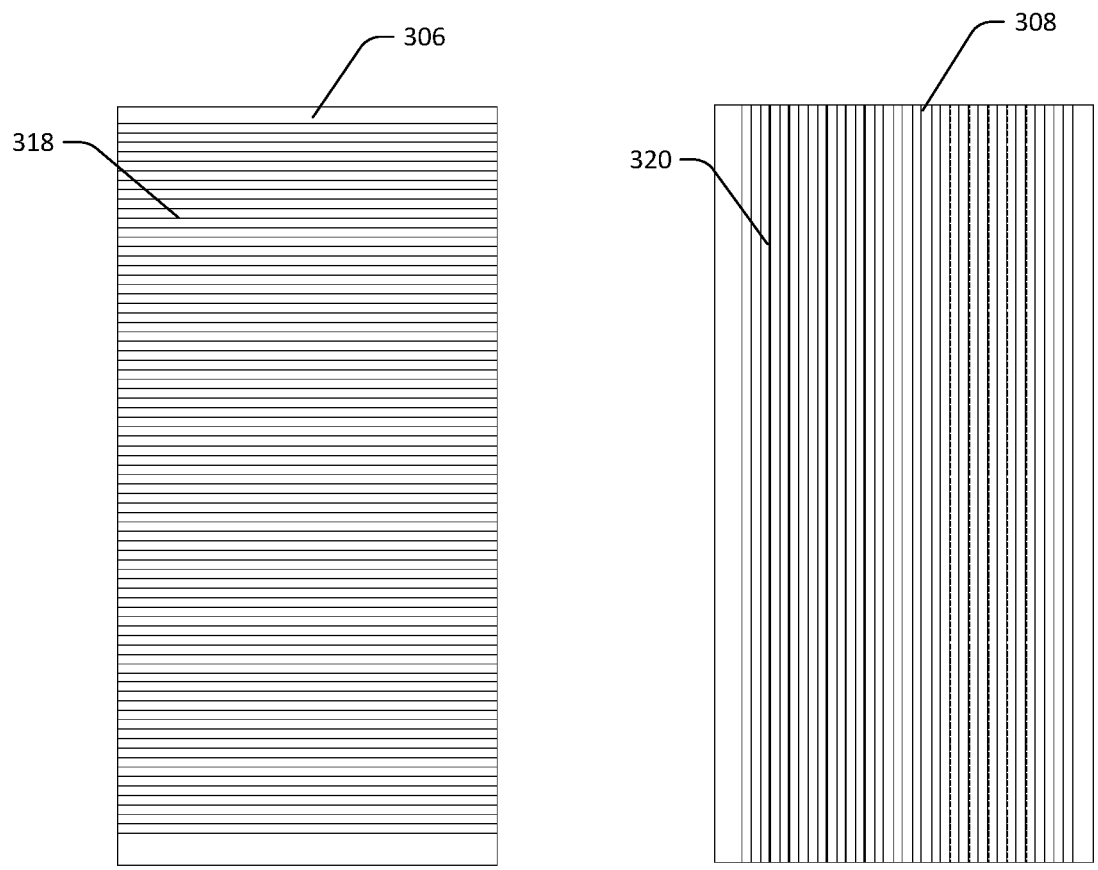
FIG. 19 illustrates plan views of two sub-layers of electrically conductive elements extending in perpendicular arrays, which form part of the sensor mat system of FIGS. 16 to 18.

Referring to FIGS. 16, 17 and 19, conductive elements 306 and 308 include a plurality of electrically conducting elements such as wires 318 and 320 distributed in parallel arrays across a non-conductive substrate. In other embodiments, wires 318 and 320 may be replaced with other conductive materials such as conductive tape, fabric, thread, paint or ink. Typical spacing of the wires is in the order of millimetres or centimetres and the spacing may be regular or irregular. The conducting wires 318 of conductive element 306 are disposed across the width of element 306 in a lateral direction while the conducting wires 320 of conductive element 308 are disposed along the length of element 308 in a longitudinal direction. As such, the wires of the two conducting elements 306 and 308 are disposed perpendicular to one another.

Piezoelectric material 304 may include any commercially available materials exhibiting the piezoresistive effect such as man-made ceramics and some semiconductor materials. Another suitable material is the Velostat™ material, which is a product manufactured by the 3M Company. Piezoresistive materials have the property that they exhibit a change in electrical resistance across the piezo material based on applied stress or pressure. In particular, their electrical resistance decreases with increasing pressure exerted on the material.

Conductive elements 307 and 308 are adhered to either side of piezoelectric material 304 by way of a non-conductive adhesive material such as polyvinyl chloride (PVC) or ethylene vinyl acetate (EVA) based polymer materials or other fabric tapes or glues. In operation, the perpendicular conducting wires 318 and 320 collectively define a grid electrode structure that, when a small electric current is passed through the wires, allows spatial sensing of pressure based on detected voltage levels across the wires. The electric current may be supplied by microcontroller 600 or another power source such as a battery or mains power.

Figure 20:
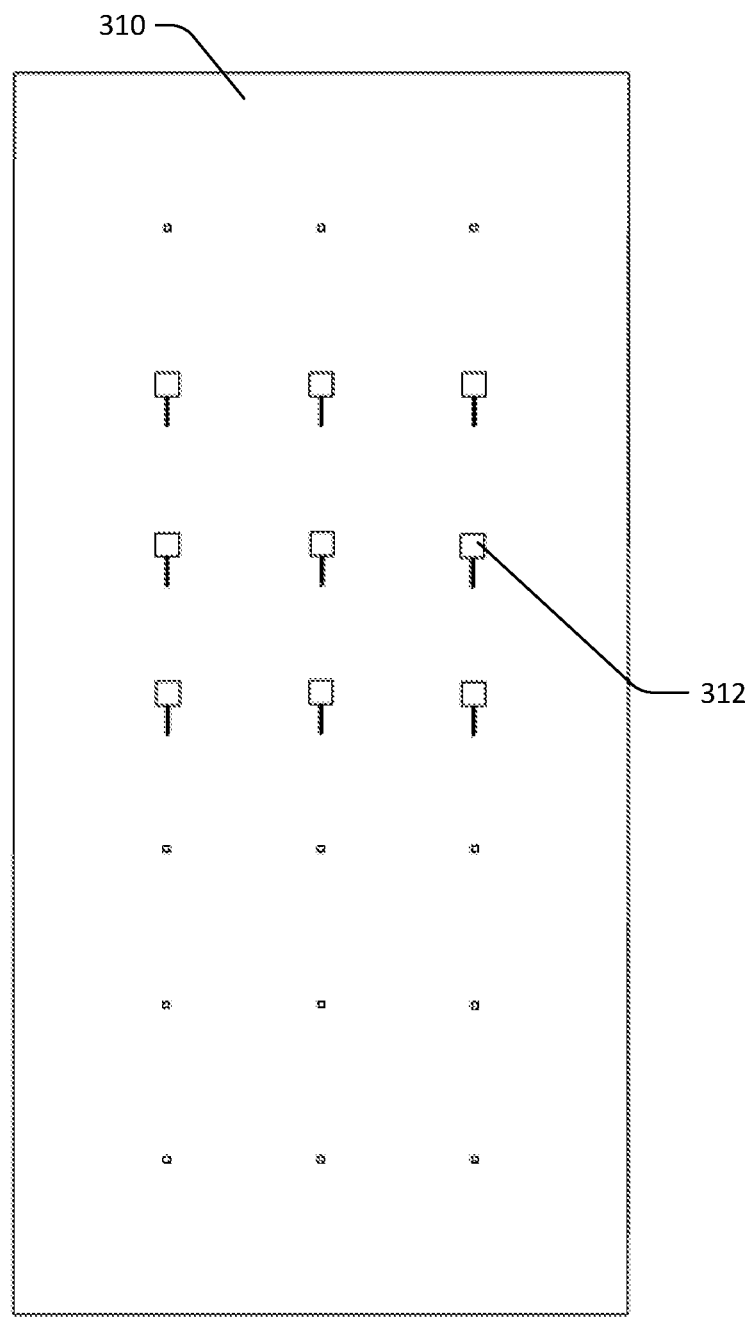
FIG. 20 is a plan view of a pressure sensor layer of the sensor mat system of FIGS. 16 to 19, the pressure sensor layer having an array of sensors embedded therein.

Referring now to FIG. 20, sensor layer 310 includes a regular array of pressure sensors 312, which may be one or more of force sensitive resistors, strain gauges, load cells, capacitive transducers and/or stretch sensors. Sensors 312 are preferably embedded within a flexible fabric material, which defines the size and shape of layer 310. This flexible fabric material may be formed of a PVC or EVA based polymer material. Although not shown, each sensor is connected to an internal electrical wire embedded within the flexible fabric material in a manner similar to an electric blanket. These internal electrical wires transmit the second pressure signals which are communicated to microcontroller 600.

The sensors of layer 310 are illustrated as being localised in a small area around a user's ilium/hip bone are, which is an area of focus for pressure sores. However, it will be appreciated that sensor layer 310 may include a wider array of sensors distributed more broadly across layer 310 and a significant number of sensors, such as 50 or 100 sensors, may be incorporated. Further, layer 301 may include sensors clustered in higher densities around particular areas of interest such as a user's shoulders, ilium/hip bone and also around the edges of layer 310 to detect potential fall events. In general, the distribution and density of sensors within layer 310 may be varied depending on the particular application and cost requirements.

The use of piezoelectric sensing layer 302 together with pressure sensor layer 310 combines the inputs of both piezoresistive materials with that of embedded force sensitive resistors (or the like) to generate a pressure map of patient movement. This combination of sensor layers gives more accurate context to piezoresistive pressure, which changes in stretch and conductance over time. This more contextualized information can be used to more accurately detect how much force is being applied at a particular location and predict user movement, heart rate, breathing rates and other physiological inputs such as muscle tone. This combination of layers also calibrates the piezoresistive layer which can change its readings over time due to stretch, which is inherent in its material properties. The more constant nature of the readings of sensor layer 310 and distances between sensors can be used to calibrate the inputs of the piezoelectric layer 302 over time.

Depending on the exact nature of the specific materials used in manufacture of piezoelectric layer 304, the layer may have different degrees of elasticity or stretch.

In addition to the layers described above, sensor mat system 300 may also include a series of elastic threads and pulleys, used in coordinated fashion similar to spring scales, to measure stretch. For example, a plurality of threads may be looped through apertures located around the periphery of sensor mat system 300 and connected to respective spring scales or strain gauges to measure stretch. Coordinated inputs from numerous spring scales can be used to generate or augment patient position and movement data.

In some embodiments, system 300 includes further layers including one or more embedded moisture sensors and/or other types of sensors to augment the pressure data. A moisture sensing layer is able to sense the presence of sweat or urine, which may be alerted to a third party.

Further devices may be incorporated with system 300 and connected to microcontroller 600 to provide more advanced functionality. For example, a combination of microphones, cameras, radar beam generators, UV detectors, thermometers and other devices combine to provide a comprehensive view of a user of system 300 at any given time. Microphones may be used for detection of snoring and other noises like slurred speech for the purpose of stroke monitoring. UV detectors are useful in informing users on ideal sleep environments.

The combination of pressure data from layers 302 and 310 provide useful inputs to allow microprocessor 600 to not only generate a pressure map of user movement, but to also perform various other advanced steps, which are described below.

In some embodiments, microcontroller 600 is configured to determine physiological signals such as breathing rate or heart rate of a subject laying on system 300 based on the pressure data received by the sensors. This may be achieved by performing a frequency analysis on the dynamic dataset relating to pressure around the area of the user's lungs and/or heart. A patient/user's breathing cycle or cardiac cycle produces regular changes in pressure and these changes can be represented as spectral signatures in the pressure data obtained by system 300. Peak frequencies can be isolated from these signals to estimate breathing and heart rates of a user.

Microcontroller 600 may also be configured to predict potential pressure sores of a user laying on system 300 based on the pressure data. For example, microprocessor 600 may be pre-programmed with predetermined pressure and time thresholds which trigger a potential pressure sore event. If a patient is imposing pressure on a particular location for a particular period of time, this may trigger an event detection. Such detection by microcontroller 600 may be based on a lookup table of data based on clinical data.

Microcontroller 600 may also be configured to detect potential fall events of a user laying on the sensor mat system based on the pressure data. If a detected pressure distribution of a patient indicates that patient is laying close to an edge of the bed, microcontroller 600 may be programmed to detect a potential fall event and optionally issue an alert to the user or third party.

In some embodiments, microcontroller 600 includes a communications module (not shown) such as an Ethernet port, Wi-Fi adaptor or Bluetooth device for transmitting the pressure data and/or other data to a remote database for further processing. For example, dynamic pressure map data may be sent to a cloud database which performs further processing. The cloud database may also be configured to perform functions like sending alerts to health professionals and loved ones of situations such as potential fall events, potential pressure sores.

Microcontroller 600 may be configured to generate a range of different third party alerts based on the pressure data. This may be performed directly by microcontroller 600 or indirectly via the cloud database and/or an associated software interface on a mobile or computer device (via a software application). Such a software interface can also provide access to third parties regarding not only alerts but also to access the pressure data, and derived physiological signal data. The software application and system may also provide insights on past potential or actual fall events, pressure sores or user movement patterns. These patterns, particularly during sleep times, can be used by microprocessor 600 or an associated remote server accessible via a cloud database to predict conditions like sleep apnoea and measure its response to treatment.

Machine learning may also be adopted by microcontroller 600 or an associated cloud server to improve alert systems and allow for remote monitoring of patients by healthcare workers or loved ones via software applications on mobile devices. Cloud server processing can also calibrate readings from system 300 via machine learning in a bidirectional manner. By way of example, a machine learning algorithm may be adopted which takes inputs from sensor mat system 300 that improves the accuracy and personalization of alerts for pressure sores, falls, emergencies such as the cessation of breathing and the accuracy and personalisation of sleep, and ergonomic posture advice over time. Suitable machine learning algorithms may include supervised or unsupervised decision trees, random forest, support vector machines, Naive Bayes classifiers, linear or logical regression or artificial neural networks. This machine learning system may also take inputs from other devices such as blood pressure monitors to provide alerts and monitoring of other diseases.

By monitoring the pressure data, prediction of more serious conditions like epilepsy and cardiac arrest can be performed locally by microprocessor 600 or remotely by a cloud server. These more advanced predictions may require a higher density of accurate sensors in the pressure sensor layer 310, particularly concentrated in areas that require it most. For example, more sensors around the chest area assists with detection of heart rate and breathing, more sensors underneath shoulders and/or hips assist with pressure sore detection, and more sensors along an edge of the bed assist with fall detection. Thus, microcontroller 600 or a cloud server may be configured to perform various signal processing functions on the pressure data like spectral analysis, data filtering, noise removal, linear regression and data interpolation.

In addition, the higher level of sensing accuracy can provide insights into sleep quality and can provide inputs in critical areas like the neck and head in patients with sleep apnoea. System 300 can provide users with insights into which pillow will suit them, detection of common pain areas, like lower back pain areas, and restless leg syndrome.

In addition to being used in a bed, system 300 may also be used in other applications such as in vehicle seats to monitor truck drivers who sit in single spaces over long periods of time.

In some embodiments, microcontroller 600 is responsive to the pressure data to selectively actuate apparatus 200 to incline or recline support arm 204 appropriately.

Inflatable Bladder System

Referring now to FIGS. 21 and 22, there is illustrated an inflatable bladder system 400. Bladder system 400 may be used in place of, or in conjunction with a standard mattress (located either above or below the mattress), and may be used as a standalone device or in conjunction with one or both of apparatus 200 and system 300 as part of smart bed system 100. In some embodiments, bladder system 400 may be incorporated inside a mattress.

As best illustrated in FIG. 21, inflatable bladder system 400 includes a plurality of inflatable cells 402, which are divided into three vertically distributed layers 404, 406 and 408. Each layer is divided into a two dimensional horizontal array of cells to form a three dimensional grid of inflatable cells. The cells may have a common volume or may vary in volume. As illustrated, larger sized cells (e.g. 405) are provided at a head end of the system to provide additional head support. An outer casing of the bladder and inflatable cells 402 are preferably formed from a flexible polymer material such as polyurethane, polyvinyl chloride (PVC), polyvinyl alcohol (PVA) or ethylenediamine (EDA) based polymers. The outer layer of inflatable bladder system 400 may also include a fabric or other materials which provide user comfort. Different comfort models may be made of different material.

It will be appreciated that the particular number of inflatable cells is variable and, in other embodiments, fewer or greater numbers of layers or numbers of cells within layers may be included. By way of example, the number of inflatable cells may range from 16 to 300.

System 400 also includes a gas delivery system 410, illustrated best in FIG. 22, for selectively delivering gas from a gas supply source 412 to the inflatable cells 402. Gas supply system 410 includes a pump 414 connected to the gas supply source 412 for delivering the gas to a plurality of gas supply lines (e.g. 416). In the illustrated embodiment, a single gas supply line 418 is connected between pump 414 and a pump manifold 420. Manifold 420 includes a plurality of electrically actuatable solenoid valves 422 disposed on respective ones of the gas supply lines 416 and being responsive to electrical control signals for selectively opening or closing the valves to deliver gas to the inflatable cells 402. Each cell 402 includes a pressure sensitive valve 421 for allowing ingress of gas but restricting back flow into the gas supply lines 416. In other embodiments, gas delivery system 410 may be replaced by an equivalent fluid delivery system to selectively deliver a fluid such as water to system 400.

Finally, inflatable bladder system 400 includes an inflation microcontroller 600 configured to generate the electrical control signals to control the selective inflation of the inflatable cells 402. Microcontroller 600 is illustrated as being the same as that of apparatus 200 and system 300 described above. However, in some embodiments, separate microcontrollers may be used. The control signals are sent to solenoid valves 422 via control line 424. Microcontroller 600 also controls the activation and deactivation of pump 414 by control line 426 in conjunction with controlling solenoid valves 422.

Pump 414, microcontroller 600, manifold 420 and solenoid valves 422 are preferably integrated within a pump and controller housing (not shown) located adjacent system 400. Where bladder system 400 is disposed beneath a mattress, the adjacent mattress may have incisions or perforations made in the bottom in alignment with cells, depending on make and model, to permit the filling of an air chamber to an associated lift, while making the lift more uniform.

In some embodiments, inflatable bladder system 400 includes a rigid or semi-rigid layer disposed beneath the plurality of inflatable cells to provide structural support. Inflatable bladder system 400 may also include engagement straps (not shown) configured to engage the inflatable bladder system with a mattress or bed frame. An elastic sheet may be applied to lie above inflatable bladder system 400 to minimise a risk of crinkle formation that could create pressure sores. A specific designed mattress may overlay bladder system 400 which is designed to minimise pressure points that may cause pressure sores. This is achieved using materials, primarily foams, of varying densities for different segments. For example, a soft but thick layer is used in regions proximal to the start of the lift, to allow for bed to bend, whilst a harder foam is used to support the small of the back, about 10 cm into the bed.

Preferably the gas is air and the gas supply source 412 includes a simple air intake on pump 414. However, it will be appreciated that inflatable bladder system 400 may utilise other types of gas or fluids.

In operation, cells 402 of inflatable bladder system 400 are inflated by microcontroller 600 issuing control signals to solenoid valves 422 along control line 424 and to pump 414 along control line 426. The control signals indicate which solenoid valves should be opened, and may also indicate other parameters such as:

- A desired time to open solenoid valves 422 and activate pump 414.
- A desired pressure for which different cells 402 should be inflated.
- A desire pressure that pump 414 should deliver air to manifold 420.
- A desired speed/power to activate pump 414.
- A desired volume of air to be delivered to different cells 402.

Upon activation of pump 414, air is sourced from gas supply source 412 and delivered to manifold 420 at a first pressure. Depending on which solenoid valves 422 are open, air is delivered along the corresponding gas supply lines 416 to desired cells 402 at a second pressure higher than the first pressure. Once the desired amount of gas is delivered, solenoid valves 422 are closed and pump 414 deactivated. The pressure sensitive valves 421 of each cell ensure the gas is maintained within the cells at the desired pressure.

To deflate cells of system 400 microcontroller 600 sends control signals along control line 424 to open particular solenoid valves 422 corresponding to the desired cells while activating pump 414 via control line 426 in a reverse mode. However, in other embodiments, alternative deflation means may be utilized. For example, microcontroller 600 may also control separate deflation valves in cells 402 to perform deflation.

In the manner described above, each cell 402 can be individually inflated and deflated to one of a plurality of predefined pressure levels. In other embodiments, the inflatable cells 402 are divided into groups and each group has a corresponding electrically actuatable solenoid valve 422 common to that group. In this manner, when a solenoid valve 422 is opened by microcontroller 600, gas is supplied equally along a common gas supply line to each of the cells within the group or along separate gas lines common to that solenoid valve. Furthermore, some or all of the inflatable cells within a group may be separated by internal electronic or pressure sensitive valves which permit flow of gas from a first cell to a second cell in the group upon the first cell reaching a predefined pressure threshold. For example, a group may comprise the three vertically adjacent cells in layers 404, 406 and 408. Gas may be delivered directly to a cell in layer 404 by a dedicated supply line, once this cell reaches a predefined threshold, an internal pressure valve (not shown) is activated and air is distributed to the cell immediately below in layer 406. A similar process may occur between the cells in layers 406 and 408. In some embodiments, the internal valves may be controlled by microcontroller 600 to provide advanced flow of air between cells.

In other embodiments, gas delivery system 410 does not include manifold 420 and gas supply lines 416 are directly connected between pump 414 and cells 402.

The electrical control signals may be provided by user input through remote control device 700 or a control panel associated with inflatable bladder system 400. A user may also be able to provide input via voice commands to a microphone (not shown). For example, a user may be able to select from one of a plurality of different predefined inflation settings in which different combinations of cells are inflated or partially inflated. The remote control device 700 may include a touchscreen display providing a visual representation of inflatable bladder system 400 and allowing a user to select cells for inflation.

In some embodiments, the electrical control signals are based on the pressure data received from system 300 described above. In this manner, inflation of the bladder is controlled based on patient position and movements detected by sensor mat system 300. In embodiments where the inflation microcontroller is different from the sensor microcontroller, the sensor microcontroller 600 is configured to transmit the pressure data to the inflation microcontroller to control inflation of the bladder based on patient position and movements.

Electrical control signals may also be provided from survey inputs from health experts (who may assess if someone is at higher risk of a pressure sore), or via a machine learning system which learns which positioning patterns seem to make for the higher comfort, or safety.

By integrating control of sensor mat system 300 and inflatable bladder system 400, microcontroller 600 can direct inflation of various cells to manipulate a users' position in order to minimise pressure sustained and avoid pressure sores. Past pressure data obtained from sensor mat system 300 may be processed in conjunction with current or past inflation status information from inflatable bladder system 400 (via electronic control signals) to direct further inflation patterns. This processing may be performed by microprocessor 600 or by an external cloud server.

As mentioned above, microprocessor 600 or an external cloud server may leverage a machine learning protocol which takes inputs from sensor mat system 300 and determines suitable control signals for system 400 to reduce the instance of pressure sores, falls, and emergencies such as the cessation of breathing, as well as improving sleep quality and ergonomic posture advice over time. This machine learning may take inputs from patients, users, or healthcare professionals to add more accuracy, and further personalize alerts and advice given. Inputs from other devices such as blood pressure monitors may be leveraged to provide additional context for dynamically adjusting system 400 appropriately.

Dynamic adjustment of inflation patterns of cells 402 provides for:
- Performing massaging functions to massage out deep vein clots of a user or massage immobile muscles.
- Shifting pressure points on a user to reduce the instance of pressure sores.
- Creating a barrier around an edge of the bed to reduce the chance of falls.
- Assisting in the movement of a user such as helping them sit up in bed.
- Adjusting neck support by adjusting the pressure of the larger cells 405 to provide extra lift behind head area.
- Providing comfort for users with back problems, or for otherwise well individuals who may find relief and better sleep from having support in certain areas.
- Providing ergonomic support for people in bed (or in chairs), as guided by pressure sensors or user inputs.

In addition to being integrated with system 300, inflatable bladder system may also operate in conjunction with inclinable bed apparatus 200. In this manner, the particular inflation pattern applied across cells 402 may take into account whether the user is in a prone or supine laying position, an inclined position or a seated upright position.

Furthermore, microcontroller 600 may take into account electronic control signals to provide insight into a current state of inflation of the bladder when determining a pressure distribution of the user by sensor system 300. Thus, the pressure data may be generated based on the received electronic control signals.

In some embodiments, microcontroller 600 is responsive to a CPR override signal to deflate all inflatable cells. This override signal may be received by an associated master override button or may be derived from the pressure data where a predefine cardiac arrest event is detected.

Figure 32:
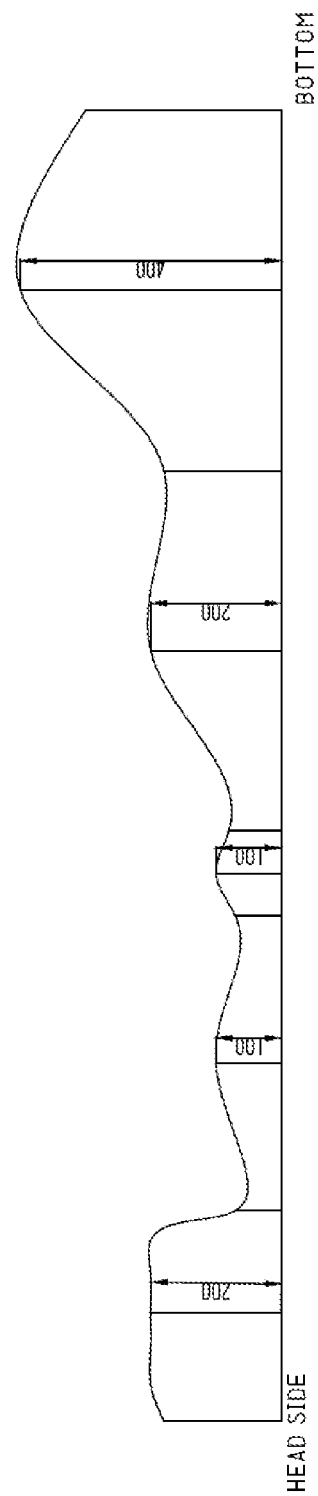
FIG. 32 is a side view of the first example profile of FIGS. 28 and 29 illustrating exemplary dimensions.
Figure 33:
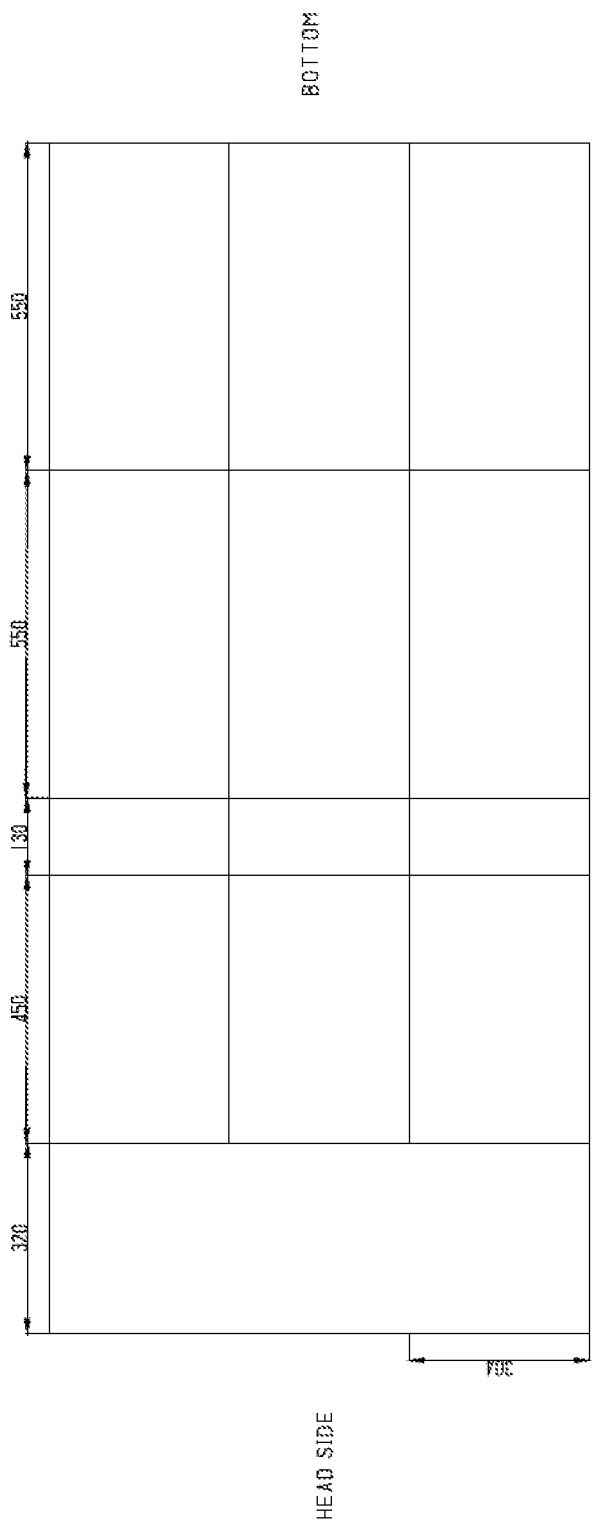
FIG. 33 is a plan view of the inflatable bladder system of FIGS. 22 and 23 illustrating exemplary dimensions of inflatable cells or groups of cells.

Exemplary inflation profiles of inflatable bladder system 400 caused by inflating different combinations of cells are illustrated in FIGS. 28 to 33. FIGS. 28, 29, 32 and 33 relate to a first exemplary inflation profile while FIGS. 30 and 31 relate to a second exemplary inflation profile. Example bladder dimensions are illustrated in FIGS. 32 and 33.

When inflatable bladder system 400 is used in conjunction with sensor mat system 300, a plastic, metal, wood or fabric sheet may be placed below system 400 which provides resistance to allow for sensors of sensor mat system 300 to accurately map position and movement of a user.

Retractable Bed Rail System

Referring now to FIGS. 25 to 27, there is illustrated a support rail system 900 for a bed. Support rail system 900 includes an engagement formation 902 for engaging with a bed frame 901. Engagement formation 902 includes an engagement arm 904 that extends substantially horizontally to be positioned under a mattress 903 of the bed, as best illustrated in FIG. 27. As illustrated, engagement arm 904 is formed of a substantially rectangular frame including parallel members 906 and 908 interconnected by parallel members 910 and 912. However, in other embodiments, engagement formation 902 may be formed of a single substantially planar panel, a pair of engagement arms or other engagement means. In some embodiments, members 906 and 908 are telescopically extendible in length to extend across different widths of mattress 903.

Support rail system 900 also includes a support rail 914 mounted to engagement formation 902 on or adjacent member 910. Support rail 914 extends substantially vertically in the operable position and is telescopically adjustable in height between two or more height positions. Telescopic adjustment is performed via a pair of telescopic arms 916 and 918, which include two or more telescopically sleeved elements of slightly different diameter that slide relative to one another along a sliding axis. Although not shown, telescopic arms 916 and 918 are operable to lock into one of a number of height positions through a locking pin (not shown) and series of longitudinally displaced locking apertures (also not shown). The locking pin is releasably engageable with a locking aperture through a corresponding release mechanism (not shown) in a similar manner to a telescopic handle of a travel case. In other embodiments, telescopic arms 916 and 918 are electronically adjustable by an electronic actuator responsive to a control signal (e.g. Bluetooth, voice command, Wi-Fi) received from microcontroller 600 or other control device.

Support rail 914 is in the form of substantially planar vertical panel 920 having a flat lower edge 922 and a curved upper edge 924. Support rail 914 also includes apertures 926 to 928 to provide hand holds for vertically extending or retracting the rail.

Support rail 914 is rotatable relative to engagement formation 902 between an operable position illustrated in FIGS. 25 to 27 and a folded position via hinge joints 930 and 932. Rotation may be performed manually by way of a rotation release mechanism (not shown). However, in other embodiments, support rail 914 is electronically rotatable by an electronic actuator responsive to a control signal (e.g. Bluetooth, voice command, Wi-Fi) issued by microcontroller 600 or other control device.

Finally, a pair of support legs 934 and 936 extend substantially downward and slightly outward from engagement formation 902 at angles in the range of 15 to 75 degrees with respect to vertical. However, in other embodiments, support legs 934 and 936 are disposed substantially vertically downward. Support legs 934 and 936 are adjustable in length to engage with a floor adjacent the bed to maintain support rail 914 in the operable position against mattress 903. Each support leg includes an abutment formation 938 and 940 formed of rubber or a similar material to provide a frictional engagement with the floor. This frictional engagement, together with the slight outward inclination of support legs 934 and 936 provide a sufficient force to retain a user in the bed even when their weight is applied against support rail 914.

Support legs 934 and 936 are formed of a plurality of telescopically sleeved elements (e.g. 942 and 944) to facilitate the legs being telescopically adjustable in length. This allows the legs to be adjustable for different height beds.

Like telescopic arms 916 and 918 described above, telescopic adjustment of support legs 934 and 936 is performed by manually actuating a releasable locking pin (not shown) into one of a series of longitudinally displaced locking apertures (also not shown) to lock the legs into one of a number of height positions. The locking pin is releasably engageable with a locking aperture through a corresponding release mechanism (not shown) in a similar manner to a telescopic handle of a travel case. In some embodiments, actuation of the locking pin may be performed electronically by an electronic actuator responsive to a control signal (e.g. Bluetooth, voice command, Wi-Fi) from microcontroller 600 or similar control device.

The various components of support rail system 900 may be formed of plastics, metal or other rigid materials.

In operation, support rail system 900 may be positioned along a side of a bed or at the head or foot of a bed. System 900 may be associated with inclining bed apparatus 200 by a flexible sheet or Velcro and/or other materials which attach the surface layers to system 900. Multiple support rail systems may be used in conjunction with one another to provide support to a user around multiple sides/ends of a bed. When installed in the operative position, support rail system 900 leverages the weight of mattress 903 with a user's weight applied thereon to reduce chances of falling.

To exit a bed, a user folds support rail 914 into the folded position wherein the support rail extends substantially vertically downward adjacent support legs 934 and 936. In some embodiments, support rail 914 may be detachable from support formation 902 to allow a user to exit a bed. Support rail 914 may be folded down manually by activation of a button (as described above), by a voice command, or by remote control by a user or healthcare worker, via central app in communication with microcontroller 600. Support legs 934 and 936 may also retract when support rail 914 is moved from the operative position to the storage position. The legs can fold to a position that places them next to support rail 914 to reduce the risk of a user falling or tripping on the legs as they exit the bed.

It will be appreciated that, in other embodiments, support rail system 900 includes only a single support leg or more than two support legs. In another embodiment, support rail system 900 includes additional features such as an associated tray table, bottle/cup holder and/or electrical charging ports for charging electrical devices while the user is in bed.

Conclusions

The above described system provides an affordable alternative bed system to assist patients recover from injuries and reduce the instances of falls and bed sores. Although described separately, each of the above aspects of the invention can be configured into a single smart bed system. The smart bed system can be used to:

Lift patients or frail people to provide them with safety and comfort around the home.

Lift people who want to work or use laptops in bed comfortably and reduce their chances of work related illnesses by doing so.

Lift people with sleep issues up in differing amounts (as determined by an associated software algorithm or application) to provide them with incline sleep therapy.

Reduce preventable incidents like falls and bed sores.

Speed up recovery and reduces overall hospital time.

When installed on an existing bed frame, the above described inclinable bed system bed more easily allows disabled patients to move around. As it is not a spring-based design, there are fewer mechanical parts that are subject to wear and tear. The actuatable bladder system provides increased patient comfort and a higher degree of adjustment via user input from a remote control, voice input and/or feedback from the sensor system.

The smart bed system is also able to connect to other devices and sensors from monitoring equipment to smart lights/blinds via the microcontroller.

Interpretation

Unless specifically stated otherwise, as apparent from the following discussions, it is appreciated that throughout the specification discussions utilizing terms such as "processing," "computing," "calculating," "determining", analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Reference throughout this specification to "one embodiment", "some embodiments" or "an embodiment" means that a particular feature, structure or characteristic described in connection with the embodiment is included in at least one embodiment of the present disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms comprising, comprised of or which comprises is an open term that means including at least the elements/features that follow, but not excluding others. Thus, the term comprising, when used in the claims, should not be interpreted as being imitative to the means or elements or steps listed thereafter. For example, the scope of the expression a device comprising A and B should not be limited to devices consisting only of elements A and B. Any one of the terms including or which includes or that includes as used herein is also an open term that also means including at least the elements/features that follow the term, but not excluding others. Thus, including is synonymous with and means comprising.

It should be appreciated that in the above description of exemplary embodiments of the disclosure, various features of the disclosure are sometimes grouped together in a single embodiment, FIG., or description thereof for the purpose of streamlining the disclosure and aiding in the understanding of one or more of the various inventive aspects. This method of disclosure, however, is not to be interpreted as reflecting an intention that the claims require more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this disclosure.

Furthermore, while some embodiments described herein include some, but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, well-known methods, structures and techniques have not been shown in detail in order not to obscure an understanding of this description.

Similarly, it is to be noticed that the term coupled, when used in the claims, should not be interpreted as being limited to direct connections only. The terms "coupled" and "connected," along with their derivatives, may be used. It should be understood that these terms are not intended as synonyms for each other. Thus, the scope of the expression a device A coupled to a device B should not be limited to devices or systems wherein an output of device A is directly connected to an input of device B. It means that there exists a path between an output of A and an input of B which may be a path including other devices or means. "Coupled" may mean that two or more elements are either in direct physical, electrical or optical contact, or that two or more elements are not in direct contact with each other but yet still co-operate or interact with each other.

Embodiments described herein are intended to cover any adaptations or variations of the present invention. Although the present invention has been described and explained in terms of particular exemplary embodiments, one skilled in the art will realize that additional embodiments can be readily envisioned that are within the scope of the present invention.

What is claimed is:

1. A sensor mat system for a bed, the sensor mat system including:
   a first layer including a piezoelectric or piezoresistive material surrounded by a plurality of electrically conductive elements configured to generate first pressure signals in response to an applied pressure, wherein the first pressure signals are indicative of a change in conductance due to stretch of the piezoelectric or piezoresistive material;
   a second layer including a plurality of spatially distributed sensors configured to generate second pressure signals in response to the applied pressure, wherein the spatially distributed sensors include force sensitive resistors, strain gauges, load cells and/or stretch sensors adapted to measure stretch, the second layer disposed between the first layer and one or more adjustable features of the bed; and
   a processor in communication with the electrically conductive elements and the sensors to:
      combine the first and second pressure signals to generate pressure data indicative of a spatial distribution of pressure across the sensor mat system;
      process the pressure data to determine a position, movement patterns, and physiological signals of a subject or object on the sensor mat system;
      calibrate the first pressure signals from the first layer based on the second pressure signals from the second layer to account for changes in stretch in the first layer over time; and
      transmit the pressure data to a controller, the controller directing adjustment of the one or more adjustable features of the bed based on the pressure data.

2. The sensor mat system according to claim 1, further comprising a gel material disposed between the first layer and the second layer.

3. The sensor mat system according to claim 1, wherein the processor is configured to access predetermined pressure and time thresholds to predict potential pressure sores of a subject laying on the sensor mat system based on the pressure data.

4. The sensor mat system according to claim 1, wherein the processor is configured to detect potential fall events of a subject laying on the sensor mat system based on the pressure data indicating that the subject is close to an edge of the bed.

5. The sensor mat system according to claim 1, further including a third layer including one or more embedded moisture sensors.

6. The sensor mat system according to claim 1, wherein the processor is configured to generate alerts based on the pressure data.

7. The sensor mat system according to claim 1, wherein:
the one or more adjustable features of the bed comprises an inflatable bladder system having a plurality of inflatable cells;
the controller is an inflation microcontroller of the inflatable bladder system; and
the processor is configured to transmit the pressure data to the inflation microcontroller to control inflation of the inflatable bladder system, using electrical control signals that are based on the pressure data.

8. The sensor mat system according to claim 1, wherein the physiological signals of the subject include a heart rate of the subject and/or a breathing rate of the subject.

9. The sensor mat system according to claim 1, wherein the processor is configured to determine the physiological signals by performing a spectral analysis of the pressure data.

10. The sensor mat system according to claim 1, wherein the processor is configured to predict a subject health condition based on the pressure data.

11. The sensor mat system according to claim 10, wherein the subject health condition includes at least one of sleep apnea, cardiac arrest, back pain, or epilepsy.

12. The sensor mat system according to claim 1, wherein the second layer further includes one or more of a temperature sensor or an ultraviolet sensor.

13. The sensor mat system according to claim 1, further comprising one or more of a camera, a UV detector, or a radar beam generator communicatively coupled to the processor.

14. The sensor mat system according to claim 1 wherein the processor is configured to connect to a cloud based system which utilizes an algorithm to complete one or more of the following:
provide alerts for pressure sore detection based on the pressure data;
provide alerts for falls detection based on the pressure data;
provide alerts for adverse conditions associated with lower breath rates based on the pressure data;
provide alerts for adverse conditions associated with fluctuating heart rates based on the pressure data; or
monitor sleep patterns based on the pressure data.

15. The sensor mat system according to claim 1, wherein the first layer is formed of three individual sub-layers comprising the piezoelectric or piezoresistive material, an upper layer of electrically conductive elements and a lower layer of electrically conductive elements, wherein the individual sub-layers are adhered together to form a single layer.

16. The sensor mat system according to claim 1, wherein the processor is adapted to generate the pressure data as a function of time to perform time dependent and historical analysis to determine subject movement patterns.

17. A bed system including:
an inclinable bed apparatus having an inclinable support arm; and
a sensor mat system disposed on the inclinable bed apparatus, the sensor mat system comprising:
a first layer including a piezoelectric or piezoresistive material surrounded by a plurality of electrically conductive elements configured to generate first pressure signals in response to an applied pressure, wherein the first pressure signals are indicative of a change in conductance due to stretch of the piezoelectric or piezoresistive material,
a second layer disposed on the plurality of electrically conductive elements of the first layer, the second layer including a plurality of spatially distributed sensors configured to generate second pressure signals in response to the applied pressure, wherein the spatially distributed sensors include force sensitive resistors. strain gauges, load cells and/or stretch sensors adapted to measure stretch, the second layer disposed between the first layer and the inclinable support arm, and
a processor communicatively coupled to the first layer, the second layer, and the support arm, the processor configured to:
combine the first and second pressure signals to generate pressure data indicative of a spatial distribution of pressure across the sensor mat system,
process the pressure data to determine a position, movement patterns, and physiological signals of a subject or object on the sensor mat system,
calibrate the first pressure signals from the first layer based on the second pressure signals from the second layer to account for changes in stretch in the first layer over time, and
direct the support arm to selectively incline or recline in response to the pressure data.

18. A sensor mat system, comprising:
a pressure sensor layer comprising a plurality of spatially distributed sensors that are each configured to generate a pressure signal in response to a force applied to the sensors;
a deformable layer disposed on the pressure sensor layer;
a piezoelectric sensing layer disposed on the deformable layer, the piezoelectric sensing layer comprising a deformable piezoelectric or piezoresistive material disposed between a first electrically conductive element sub-layer and a second electrically conductive element sub-layer, the first electrically conductive element sub-layer and the second electrically conductive element sub-layer each comprising electrically conductive elements arranged in a grid configuration, the electrically conductive elements electrically coupled to a power source that provides an electric current through the electrically conductive elements and, when a drop in voltage is detected in the electric current through the electrically conductive elements due to stretch of the deformable piezoelectric or piezoresistive material, causes generation of one or more signals indicating a change in conductance of the electric current; and
a processor communicatively coupled to the sensors of the pressure sensor layer and the electrically conductive elements of the piezoelectric sensing layer, the processor configured to:

generate pressure data indicative of a spatial distribution of pressure across the sensor mat system based on the pressure signals received from each of the spatially distributed sensors of the pressure sensor layer in combination with the one or more signals from the piezoelectric sensing layer, determine a position, movement patterns, and physiological signals of a subject or object on the sensor mat system from the generated pressure data, and calibrate the one or more signals generated by the piezoelectric sensing layer based on the pressure signals received from each of the spatially distributed sensors of the pressure sensor layer to account for changes in stretch of the deformable piezoelectric or piezoresistive material over time.

19. The sensor mat system of claim 18, wherein the electrically conductive elements comprise a plurality of wires distributed in parallel arrays across a non-conductive substrate.

20. The sensor mat system of claim 18, wherein the deformable piezoelectric or piezoresistive material is adhered to the first and second electrically conductive element sub-layers via a non-conductive adhesive material.

21. The sensor mat system of claim 18, wherein the plurality of spatially distributed sensors are embedded within a flexible fabric material comprising one or more wires that electrically interconnects each of the plurality of spatially distributed sensors.

* * * * *